(12) United States Patent
Bailly et al.

(10) Patent No.: US 8,796,489 B2
(45) Date of Patent: Aug. 5, 2014

(54) KETOBENZOFURAN DERIVATIVES, METHOD FOR SYNTHESIZING SAME, AND INTERMEDIATES

(75) Inventors: Frédéric Bailly, Paris (FR); Bernard Grimaud, Paris (FR); Irina Malejonock, Paris (FR); Philippe Vayron, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/599,374

(22) Filed: Aug. 30, 2012

(65) Prior Publication Data
US 2013/0012729 A1      Jan. 10, 2013

Related U.S. Application Data

(63) Continuation of application No. PCT/FR2011/050420, filed on Mar. 1, 2011.

(30) Foreign Application Priority Data

Mar. 2, 2010   (FR) ...................................... 10 51510

(51) Int. Cl.
| C07C 211/00 | (2006.01) |
| C07C 215/00 | (2006.01) |
| C07C 205/00 | (2006.01) |
| C07C 207/00 | (2006.01) |

(52) U.S. Cl.
USPC ............................ 564/305; 564/443; 568/306

(58) Field of Classification Search
CPC ............................. C07D 331/02; C07D 307/00
See application file for complete search history.

(56) References Cited

U.S. PATENT DOCUMENTS

| 4,243,405 | A | * | 1/1981 | Balasubramanyan et al. ............................ 504/181 |
| 5,066,803 | A | | 11/1991 | D'Ambra et al. |
| 5,223,510 | A | | 6/1993 | Gubin et al. |
| 6,828,448 | B2 | | 12/2004 | Fino et al. |
| 6,846,936 | B2 | | 1/2005 | Biard |
| 2012/0065411 | A1 | | 3/2012 | Kretzschmar et al. |
| 2012/0077995 | A1 | | 3/2012 | Kretzschmar et al. |
| 2012/0289717 | A1 | | 11/2012 | Friesz et al. |
| 2012/0330036 | A1 | | 12/2012 | Friesz et al. |
| 2013/0023677 | A1 | | 1/2013 | Bon et al. |
| 2013/0023678 | A1 | | 1/2013 | Priem et al. |

FOREIGN PATENT DOCUMENTS

| EP | 0471609 A1 | 2/1992 |
| WO | WO 2007/100295 A1 | 9/2007 |
| WO | WO 2009/044143 A2 | 4/2009 |
| WO | WO 2012/127173 | 9/2012 |
| WO | WO 2012/131408 | 10/2012 |
| WO | WO 2012/131409 | 10/2012 |
| WO | WO 2012/131410 | 10/2012 |
| WO | WO 2013/014478 | 1/2013 |
| WO | WO 2013/014479 | 1/2013 |
| WO | WO 2013/014480 | 1/2013 |

OTHER PUBLICATIONS

Fehnel, EA. Quinoline Analogs of Podophyllotoxin. I. Preliminary Experiments. Syntheses of Some 4-Phenylquinoline Derivatives. J. Org. Chem. 1958, vol. 23, p. 433, left column, compound V.*
Batra, S. et al. Syntheses and Biological Evaluation of Alkanediamines as Antioxidant and Hypolipidemic Agents. Bioorganic & Medicinal Chemistry. 2001, vol. 9, p. 3094, compounds 2-5, c-f.*
Joshi, KC. et al. Synthesis and Reactivity in Inorganic and Metal-Organic Chemistry. Synth. React. Inorg. Met.—Org. Chem. 1986, vol. 16(7), p. 1012, table 1, compound Nos. 5-7.*
Mehrotra, PK. et al. Search for new chemical entities as menses inducing agents. Contraception. 2003, vol. 64, p. 187, figure 1.*
Kwiatkowski, E. et al. Metal Benzoylpivaloylmethanates, Part I. Free Ligands and Copper(II) Chelates. Transition Met. Chem. 1978, vol. 3, p. 306, table 1, compounds 2-3.*
Batra, S. et al. Syntheses and Biological Evaluation of Alkanediamines as Antioxidant and Hypolipidemic Agents. Bioorganic & Medicinal Chemistry. 2001, vol. 9, p. 3094.*
Joshi, KC. et al. Synthesis and Reactivity in Inorganic and Metal-Organic Chemistry. Synth. React. Inorg. Met.—Org. Chem. 1986, vol. 16(7), p. 1012.*
Mehrotra, PK. et al. Search for new chemical entities as menses inducing agents. Contraception. 2003, vol. 64, p. 187.*
Kwiatkowski, E. et al. Metal Benzoylpivaloylmethanates, Part I. Free Ligands and Copper(II) Chelates. Transition Met. Chem. 1978, vol. 3, p. 306.*

(Continued)

*Primary Examiner* — Janet L Andres
*Assistant Examiner* — Ben S Michelson
(74) *Attorney, Agent, or Firm* — Scully, Scott, Murphy & Presser P.C.

(57) ABSTRACT

The present disclosure relates to ketobenzofuran derivatives of the general formula (I):

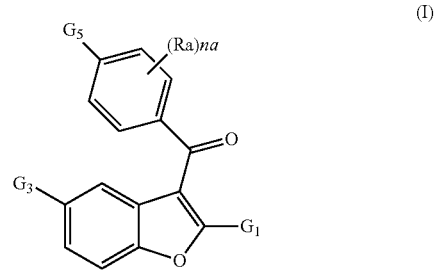

as well as to a method of synthesizing the same by coupling a quinonimine and an enaminone by a Nenitzescu reaction and to the intermediates of the synthesis thereof.

1 Claim, No Drawings

(56) References Cited

OTHER PUBLICATIONS

Krongauz, ES. et al. Poly(anilophenylquinoxaline)s. Inst. Elementoorg. Soedin. 1986, vol. 28(4), p. 771.*

Hauser, CR. et al. Alkaline cleavage of unsymmetrical β-diketones. Ring opening of acylcyclohexanones to form ε-acylcaproic acids. Journal of the American Chemical Society. 1948, vol. 70, p. 4025.*

Adams, R. et al. Quinone imides. IV. P-Quinone monosulfonimides. Journal of the American Chemical Society. 1951, vol. 73, p. 1145.*

Bartoli, G. et al. Unexpected Elimination to α,β-Alkynylketones in the Reaction of Dianions of 1-Arylenanimones with Trimethylchlorosilane. Tetrahedron Letters. 1991, vol. 32, p. 7092.*

U.S. Appl. No. 13/742,810, filed Jan. 16, 2013, Bailly, et al.

U.S. Appl. No. 13/742,816, filed Jan. 16, 2013, Bon, et al.

U.S. Appl. No. 13/711,891, filed Dec. 12, 2012, Friesz.

U.S. Appl. No. 13/740,505, filed Jan. 14, 2013, Friesz, et al.

U.S. Appl. No. 13/638,484, filed Aug. 30, 2012, Bailly, et al.

International Search Report for WO2011/107705 dated Sep. 9, 2011.

Bartoli, et al., Unexpected Elimination to α,β-Alkynylketones in the Reaction of Dianions of 1-Arylenaminones With Trimethylchlorosilane, Tetrahedron Letters, vol. 32, No. 48, pp. 7091-7092, (1991).

\* cited by examiner

KETOBENZOFURAN DERIVATIVES, METHOD FOR SYNTHESIZING SAME, AND INTERMEDIATES

This application is a continuation of International Application No. PCT/FR2011/050420, filed Mar. 1, 2011, which is incorporated herein by reference in its entirety; which claims the benefit of priority of French Patent Application No. 1051510, filed Mar. 2, 2010.

The present invention relates to ketobenzofuran derivatives of general formula (I) represented below and to their process of synthesis via the coupling between a quinoneimine and an enaminone and to their synthetic intermediates.

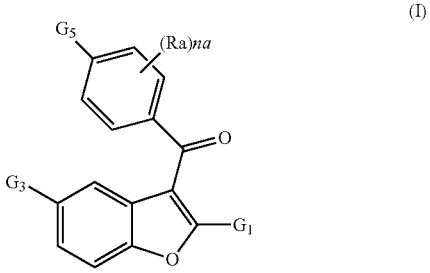

In the ketobenzofuran derivatives of formula (I),

G1 represents a linear or branched alkyl group (i), a haloalkyl group (ii), a cycloalkyl group (iii), a substituted or unsubstituted aryl group (iv), an alkene group (v) or an alkyne group (vi), G3 represents (i) an —NHSO$_2$Rc group or (ii) an —NHRc group, where Rc represents (a) a linear or branched alkyl group, (b) a cycloalkyl group or (c) a substituted or unsubstituted aryl group, G5 represents a halogen atom or an —ORb group, where Rb represents a hydrogen atom, an alkyl, haloalkyl, aryl, arylalkyl, heteroaryl, cycloalkyl or heterocycloalkyl group or an -alkyleneaminoalkyl group, Ra is chosen from a hydrogen atom, halogen atoms or alkyl, haloalkyl, alkoxy and alkoxyalkyl groups, na is an index equal to 0, 1, 2, 3 or 4.

A particularly advantageous derivative of the ketobenzofurans (I) is 2-(n-butyl)-3-[4-(3-{di(n-butyl)amino}propoxy)benzoyl]-5-(methylsulfonamido)benzofuran, known under the name of dronedarone. Dronedarone, of formula (D) below:

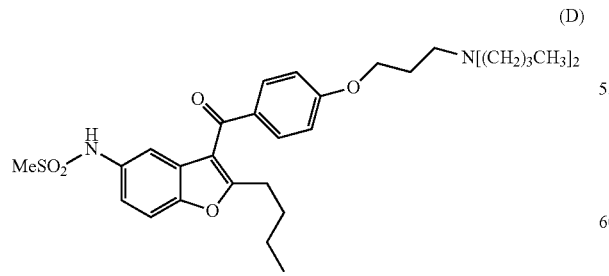

can be provided in the free base form or in the salt form, in particular in the form of the hydrochloride salt of 2-(n-butyl)-3-[4-(3-{di(n-butyl)amino}propoxy)benzoyl]-5-(methylsulfonamido)benzofuran.

Dronedarone is proving to be of particular use as active principle in cardiac arrhythmia indications.

Currently, dronedarone in the free base form is synthesized according to the process described in EP 0 471 609 B1 via the key intermediate comprising a benzofuran ring system, 2-butyl-5-nitrobenzofuran. In this synthetic process, the intermediate 2-butyl-5-nitrobenzofuran has to be functionalized in the 3 position and has to be converted in the 5 position according to Scheme 1 below. Specifically, the nitro group carried in the 5 position of 2-butyl-5-nitrobenzofuran has to be converted to methanesulfonamide by a reduction of the —NO$_2$ to give —NH$_2$, followed by a sulfonylation.

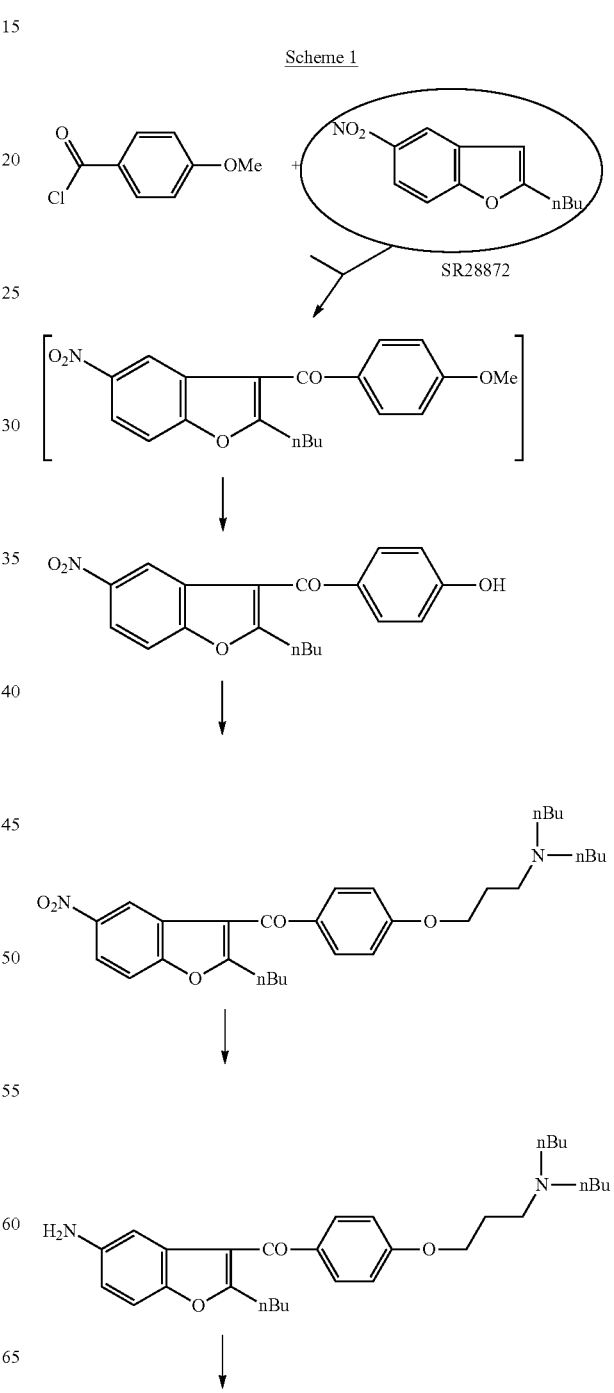

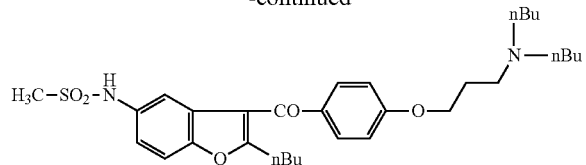

The complexity of the technical implementation of this type of process proves to be problematic and harmful in terms of yield, of safety (use of hydrogen and of an alkylating reagent during the mesylation) and of the environment (generation of iron or aluminum salts during the Friedel-Crafts stage).

The Applicant Company has thus looked for novel synthetic routes involving benzofurans, preferably already functionalized in the 2, 3 and 5 positions of the benzofuran ring system and advantageously already appropriately functionalized in the 2 and 5 positions, in order to carry out the synthesis of molecules of above formula (I), thus making it possible to circumvent the technical difficulties while meeting as best as possible the constraints of cost, of toxicity, of safety and of respect for the environment related to the industrial operation of such a synthetic process.

The Applicant Company has now found a novel process for the synthesis of ketobenzofuran derivatives of formula (I), in particular dronedarone of above formula (D) and its hydrochloride salt, comprising a Nenitzescu reaction stage involving an α,β-unsaturated ketone and a p-quinone which exhibits an excellent regioselectivity with negligible formation of the following indole (E).

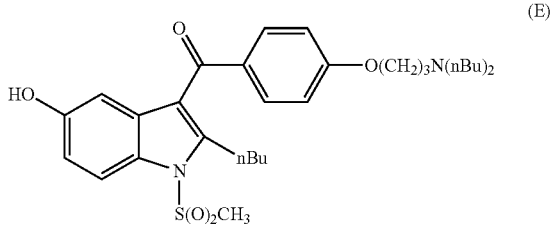

This result is all the more surprising as the regioselectivity of the Nenitzescu reaction is controlled by the hindrance of the quinonimine used: a quinonimine carrying a hindering group directs the reaction towards route A, whereas it might be expected that a group of low hindrance would direct the reaction equally well towards route A as route B, resulting in the production of a mixture of products.

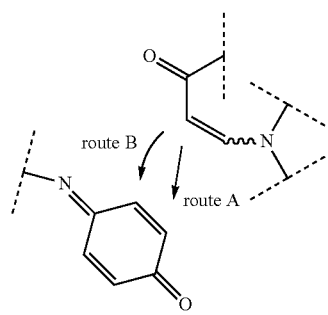

According to a first aspect, the invention is targeted at a ketobenzofuran derivative of following formula (I):

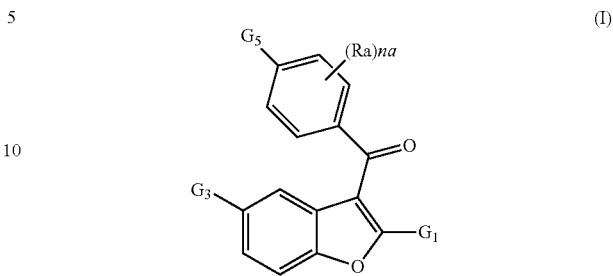

in which:

G1 represents a linear or branched alkyl group (i), advantageously a $C_1$-$C_8$ alkyl group, more advantageously still a $C_1$-$C_4$ alkyl group, such as, for example, a methyl, ethyl, n-propyl, isopropyl, n-butyl, sec-butyl or tert-butyl group, a haloalkyl group (ii), a cycloalkyl group (iii), a substituted or unsubstituted aryl group (iv), an alkene group (v) or an alkyne group (vi); advantageously, G1 represents an alkyl group and more advantageously still G1 represents an n-butyl group;

G3 represents (i) an —$NHSO_2Rc$ group or (ii) an —NHRc group, where Rc represents (a) a linear or branched alkyl group, advantageously a $C_1$-$C_8$ alkyl group, more advantageously still a $C_1$-$C_4$ alkyl group, such as, for example, a methyl, ethyl, n-propyl, isopropyl, n-butyl, sec-butyl or tert-butyl group, (b) a cycloalkyl group or (c) a substituted or unsubstituted aryl group; advantageously, G3 represents an —$NHSO_2$alkyl group or an —$NHSO_2$aryl group; more advantageously still, G3 represents an —$NHSO_2CH_3$ group;

G5 represents a halogen atom or an —ORb group, where Rb represents a hydrogen atom, an alkyl, haloalkyl, aryl, arylalkyl, heteroaryl, cycloalkyl or heterocycloalkyl group or an -alkyleneaminoalkyl group; advantageously, G5 represents an —ORb group with Rb chosen from -alkyleneaminoalkyl groups; advantageously, Rb represents a 3-(di(n-butyl)amino)propyl group;

Ra represents a substituent chosen from a hydrogen atom, halogen atoms or alkyl, haloalkyl, alkoxy and alkoxyalkyl groups; advantageously, Ra represents a substituent chosen from a hydrogen atom, halogen atoms and alkyl groups, na is an index equal to 0, 1, 2, 3 or 4, the said ketobenzofuran derivative being in the acid (i), base (ii), addition salt with an acid or with a base (iii), hydrate (iv) or solvate (v) form, with the exception of dronedarone, its salts, its solvates and its hydrates.

According to a specific aspect, the following compounds are excluded:

3-[4-(2-{di(n-butyl)amino}ethoxy)benzoyl]-2-(n-butyl)-5-(methylsulfonamido)benzofuran;

5-(n-butylsulfonamido)-3-[4-(3-{di(n-butyl)amino}propoxy)benzoyl]-2-(n-butyl)benzofuran;

2-phenyl-3-[4-(3-{di(n-butyl)amino}propoxy)benzoyl]-5-(methylsulfonamido)benzofuran;

3-[4-(3-{di(n-butyl)amino}propoxy)benzoyl]-2-isopropyl-5-(methylsulfonamido)benzofuran toluenesulfonate;

2-[4-(3-{di(n-butyl)amino}propoxy)benzoyl]-3-methyl-5-(methyl-sulfonamido)benzofuran hydrochloride;

3-[4-(5-{di(n-butyl)amino}pentoxy)benzoyl]-2-(n-butyl)-5-(methylsulfonamido)benzofuran;

3-[4-(3-{di(n-butyl)amino}propoxy)benzoyl]-2-ethyl-5-(methyl-sulfonamido)benzofuran dioxalate;

3-[4-(3-{di(n-butyl)amino}propoxy)benzoyl]-2-(n-propyl)-5-(methylsulfonamido)benzofuran;

3-[4-(3-{diethylamino}propoxy)benzoyl]-2-(n-butyl)-5-(methylsulfonamido)benzofuran;

2-(n-butyl)-3-[4-(3-{di(n-butyl)amino}propoxy)-3,5-di(tert-butyl)benzoyl]-5-(methylsulfonamido)benzofuran oxalate;

2-(n-butyl)-3-[4-(3-{di(n-butyl)amino}propoxy)-3,5-dimethylbenzoyl]-5-(methylsulfonamido)benzofuran hemioxalate;

3-[4-(3-{di(n-butyl)amino}propoxy)benzoyl]-2-(n-butyl)-5-(tolylsulfonamido)benzofuran hydrogen fumarate.

According to a second aspect, the invention is targeted at a process for the synthesis of a ketobenzofuran derivative, in the acid (i), base (ii), addition salt with an acid or with a base (iii), hydrate (iv) or solvate (v) form, advantageously dronedarone or its hydrochloride salt, the said ketobenzofuran derivative being of following formula (I):

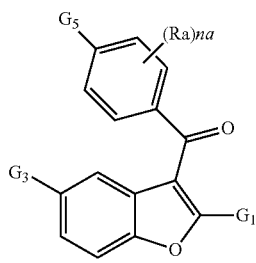

in which:

G1 represents a linear or branched alkyl group (i), advantageously a $C_1$-$C_8$ alkyl group, more advantageously still a $C_1$-$C_4$ alkyl group, such as, for example, a methyl, ethyl, n-propyl, isopropyl, n-butyl, sec-butyl or tert-butyl group, a haloalkyl group (ii), a cycloalkyl group (iii), a substituted or unsubstituted aryl group (iv), an alkene group (v) or an alkyne group (vi); advantageously, G1 represents an alkyl group and more advantageously still G1 represents an n-butyl group;

G3 represents (i) an —$NHSO_2Rc$ group or (ii) an —NHRc group, where Rc represents (a) a linear or branched alkyl group, advantageously a $C_1$-$C_8$ alkyl group, more advantageously still a $C_1$-$C_4$ alkyl group, such as, for example, a methyl, ethyl, n-propyl, isopropyl, n-butyl, sec-butyl or tert-butyl group, (b) a cycloalkyl group or (c) a substituted or unsubstituted aryl group; advantageously, G3 represents an —$NHSO_2$alkyl group or an —$NHSO_2$aryl group; more advantageously still, G3 represents an —$NHSO_2CH_3$ group;

G5 represents a halogen atom or an —ORb group, where Rb represents a hydrogen atom, an alkyl, haloalkyl, aryl, arylalkyl, heteroaryl, cycloalkyl or heterocycloalkyl group or an -alkyleneaminoalkyl group; advantageously, G5 represents an —ORb group with Rb chosen from -alkyleneaminoalkyl groups; advantageously, Rb represents a 3-(di[n-butyl]amino)propyl group;

Ra represents a substituent chosen from a hydrogen atom, halogen atoms or alkyl, haloalkyl, alkoxy and alkoxyalkyl groups; advantageously, Ra represents a substituent chosen from a hydrogen atom, halogen atoms and alkyl groups, na is an index equal to 0, 1, 2, 3 or 4, the said process comprising a Nenitzescu reaction between:

an enaminone intermediate Y-G2 of following formula (II):

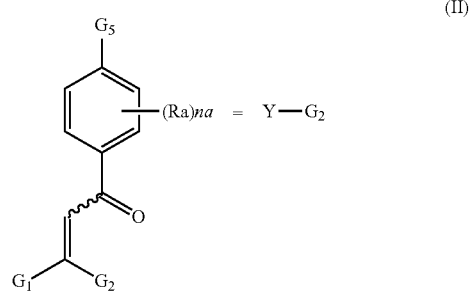

in which the groups G1 and G5, the substituent Ra and the index na are as defined above and in which the group G2 represents a group chosen from:

—NH—$(CH_2)_{nb}$—NHY groups, the said enaminone (II) then being of formula Y—NH—$(CH_2)_{nb}$—NHY, where nb represents an integer from 1 to 10, advantageously nb represents an integer from 1 to 5 and more advantageously still nb is equal to 2 or 4 and where Y has the formula as defined below:

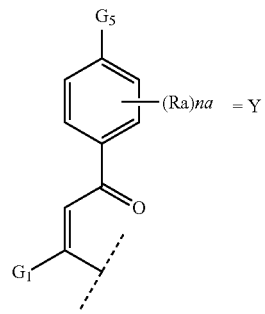

with the groups G1 and G5, the substituent Ra and the index na as defined above; advantageously, the —NH—$(CH_2)_{nb}$—NHY groups are chosen from:

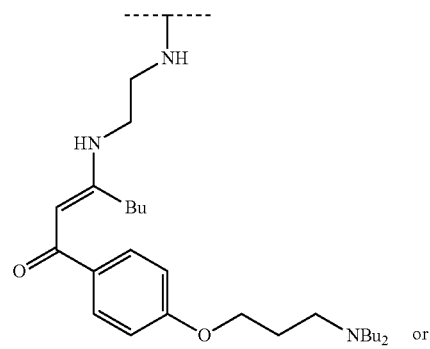

or

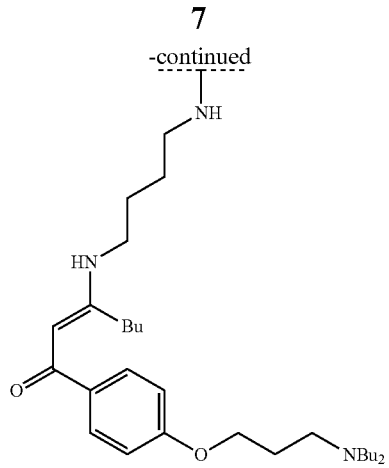

and a —NRdRe groups, the said enaminone (II) then being of formula Y—NRdRe, where Rd and Re are identical or different and are chosen, independently of one another, from a hydrogen atom, alkyl groups and aryl groups, the said aryl and alkyl groups optionally being substituted; advantageously, Rd is a hydrogen atom and Re is an aryl group substituted by an alkoxyalkyl or an alkyl group; advantageously, Re is a tert-butyl or —$C_6H_4$—$OCH_3$ group, or Rd and Re form a heterocycloalkyl with the nitrogen atom to which they are attached, and a p-quinone intermediate of formula (III):

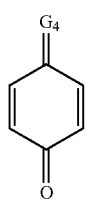

(III)

in which the group G4 is chosen from (i) =$NSO_2$alkyl groups, (ii) =$NSO_2$aryl groups and (iii) =NRc groups, where Rc is chosen from hydrogen, alkyl groups, aryl groups and haloalkyl groups; advantageously, the group G4 represents an =$NSO_2$alkyl group; more advantageously still, the group G4 represents an =$NSO_2CH_3$ group.

The compounds of formula (I) can comprise one or more asymmetric carbon atoms. They can thus exist in the form of enantiomers or of diastereoisomers. These enantiomers and diastereomers, and their mixtures, including the racemic mixtures, come within the invention.

The compounds of formula (I) can exist in the form of bases or of pharmaceutically acceptable addition salts with organic or inorganic acids. Such addition salts come within the invention. These salts can be prepared with pharmaceutically acceptable acids, but the salts of other acids, for example of use in the purification or the isolation of the compounds of formula (I), also come within the invention.

Mention may be made, as example of compounds of formula (I) in the form of salts, of the compounds of formula (I) in the form of oxalate, hydrochloride, hydrobromide, sulphate, sulphamate, phosphate, nitrate, maleate, fumarate, methanesulphonate, benzoate, ascorbate, pamoate, succinate, hexamate, bismethylenesalicylate, ethanedisulphonate, acetate, propionate, tartrate, salicylate, citrate, gluconate, lactate, malate, cinnamate, mandelate, citraconate, aspartate, palmitate, stearate, itaconate, glycolate, p-aminobenzoate, glutamate, benzenesulphonate, p-toluenesulphonate or theophyllineacetate salts and the salts formed from amino acids, such as lysine or histidine salts.

The compounds of formula (I) can also exist in the form of hydrates or solvates, namely in the form of combinations or associations with one or more molecules of water or with a solvent. Such hydrates and solvates also come within the invention.

According to one embodiment, a subject-matter of the invention is in particular a process for the synthesis of a ketosulphonamidobenzofuran derivative of formula (I') represented below:

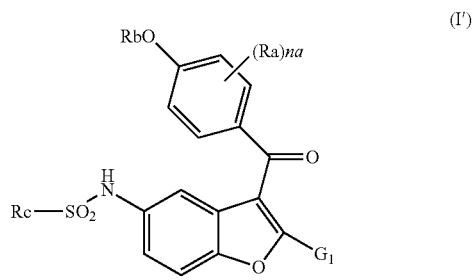

(I')

in which:

G1 represents a linear or branched alkyl group (i), advantageously a $C_1$-$C_8$ alkyl group, more advantageously still a $C_1$-$C_4$ alkyl group, such as, for example, a methyl, ethyl, n-propyl, isopropyl, n-butyl, sec-butyl or tert-butyl group, a haloalkyl group (ii), a cycloalkyl group (iii), a substituted or unsubstituted aryl group (iv), an alkene group (v) or an alkyne group (vi); advantageously, G1 represents an alkyl group and more advantageously still G1 represents a methyl or n-butyl group;

and/or

Ra is chosen from a hydrogen atom, halogen atoms or alkyl, haloalkyl, alkoxy and alkoxyalkyl groups; advantageously, Ra is chosen from a hydrogen atom, halogen atoms and alkyl groups; more advantageously still, Ra represents a hydrogen atom, and/or na is equal to 0, 1, 2, 3 or 4, and/or Rb represents a hydrogen atom, an alkyl, haloalkyl, aryl, arylalkyl, heteroaryl, cycloalkyl or heterocycloalkyl group or an -alkyleneaminoalkyl group; advantageously, Rb is chosen from a hydrogen atom, an alkyl or haloalkyl group and an -alkyleneaminoalkyl group; advantageously, Rb represents an -alkyleneaminoalkyl group chosen from an -alkylene-NRR' group or an -alkylene-$N^+$HRR' $Z^-$ group, with $Z^-$ the counteranion of the said salt as defined above; advantageously, $Z^-$ is the $Cl^-$ counteranion; with R and R', which are identical or different, chosen, independently of one another, from a hydrogen atom, aryl groups and alkyl groups; advantageously, R and R' are identical and/or R and R' are chosen from alkyls; more advantageously still, R and R' each represent an n-butyl group, advantageously, the -alkylene-NRR' group and the -alkylene-$N^+$HRR' group respectively represent a —($C_1$-$C_5$)alkylene-N[($C_1$-$C_5$)alkyl]$_2$ group and a —($C_1$-$C_5$)alkylene-$N^+$H[($C_1$-$C_5$)alkyl]$_2Z^-$ group, with Z as defined above and with —($C_1$-$C_5$)alkylene-representing —$CH_2$—, —$(CH_2)_2$—, —(CH$_2$)$_3$—, —(CH$_2$)$_4$— or —(CH$_2$)$_5$— and the —(C$_1$-C$_5$) alkyl groups, which are identical or different, representing, independently of one another, a (i) —C$_1$alkyl group, for example the methyl group, or a (ii) —C$_2$alkyl group, for example the ethyl group, a (iii) —C$_3$alkyl group, for example the n-propyl group or the isopropyl group, a (iv) —C$_4$alkyl group, for example the n-butyl, isobutyl or tert-butyl group, or a (v) —C$_5$alkyl group, for example the n-pentyl or isopentyl group, more advantageously still, Rb represents the —(CH$_2$)$_3$N[(CH$_2$)$_3$CH$_3$]$_2$ group or the —(CH$_2$)$_3$N$^+$H[(CH$_2$)$_3$CH$_3$]$_2$Cl$^-$ group, and/or Rc represents an alkyl group or an aryl group; advantageously, Rc is a methyl or phenyl group, the said process comprising a Nenitzescu reaction between an intermediate Y'-G2 of formula (II'):

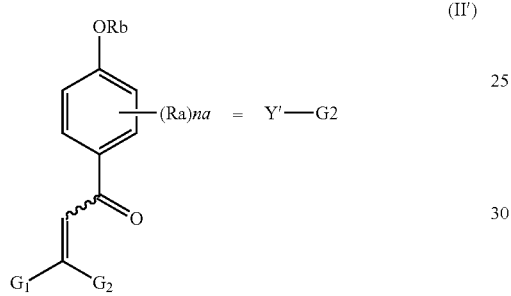

in which the groups G1, Ra and Rb and the index na are as defined above and in which the group G2 is chosen from (i) —NH—(CH$_2$)$_{nb}$—NHY' groups, with nb representing an integer from 1 to 10, advantageously an integer from 1 to 5; more advantageously still, nb is equal to 2 or 4; and Y' the part of the molecule (II') defined above, and (ii) —NRdRe groups, with Rd and Re, which are identical or different, chosen, independently from one another, from a hydrogen atom, aryl groups and alkyl groups, at least one being a hydrogen atom; advantageously, Rd is a hydrogen atom and Re is an optionally substituted aryl group or an alkyl group; advantageously, Re is a tert-butyl group; or Rd and Re form a heterocycloalkyl with the nitrogen atom to which they are attached, and an intermediate of formula (III'):

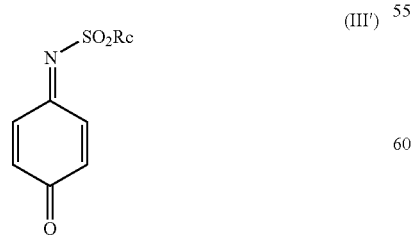

in which the group Rc is as defined above; advantageously, Rc is a methyl or phenyl group.

According to one embodiment, the group G2 of the intermediate (II') represents an —NH— tert-butyl or

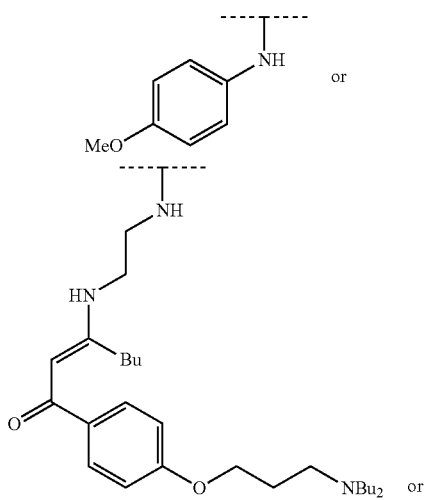

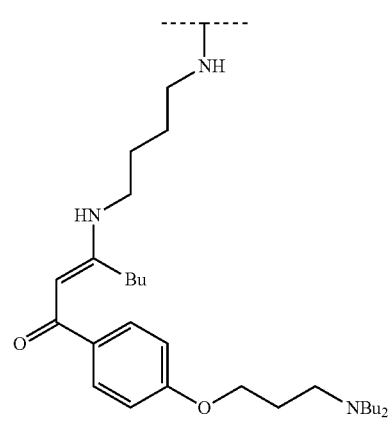

group.

According to a third aspect, the invention is also targeted at synthetic intermediates, in particular the enaminones of formula (II) where G1, G2, G5, Ra and na are as defined above and the diketones of formula (V) where G1, G5, Ra and na are as defined above:

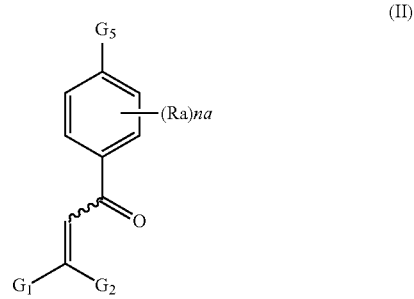

-continued

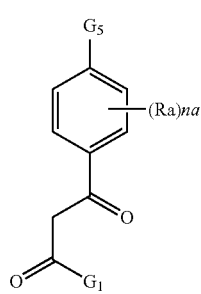
(V)

According to the invention, the synthetic intermediates are chosen from the enaminones of formula (II), where G1, G2, Ra and na are as defined in either one of claims 4 and 5 and G5 represents a halogen atom or an —ORb group, where Rb represents a hydrogen atom, a haloalkyl, aryl, arylalkyl, heteroaryl, cycloalkyl or heterocycloalkyl group or an -alkyleneaminoalkyl group;

and the diketones of formula (V), where G1, Ra and na are as defined in either one of claims 4 and 5 and G5 represents a halogen atom or an —ORb group, where Rb represents a haloalkyl, aryl, arylalkyl, heteroaryl, cycloalkyl or heterocycloalkyl group or an -alkyleneaminoalkyl group;

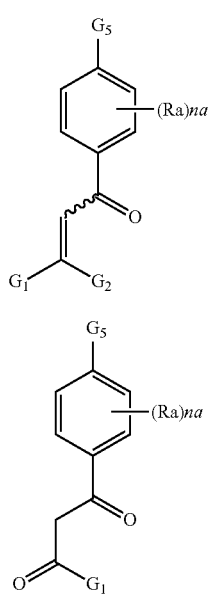

In the context of the present invention and unless otherwise mentioned in the text:

the numbering of the positions of the benzofuran ring system is understood to mean as done in the following way:

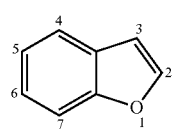

a halogen atom is understood to mean: a fluorine, chlorine, bromine or iodine atom;

an alkyl group is understood to mean: a saturated and linear or branched aliphatic group which can comprise 1, 2, 3, 4 or 5 carbon atoms (abbreviated by —($C_1$-$C_5$)alkyl). Mention may be made, as examples, as (i) —$C_1$alkyl group, of the methyl group, as (ii) —$C_2$alkyl group, of the ethyl group, as (iii) —$C_3$alkyl group, of the n-propyl group and the isopropyl group, as (iv) —$C_4$alkyl group, of the n-butyl group, the isobutyl group and the tert-butyl group, and, as (v) —$C_5$alkyl group, of the n-pentyl group and the isopentyl group;

a haloalkyl group is understood to mean: an alkyl group as defined above substituted by 1, 2, 3, 4 or 5 halogen atoms as defined above. Mention may be made, for example, of the -halo($C_1$-$C_5$)alkyl groups, with ($C_1$-$C_5$)alkyl as defined above, such as, for example, the trifluoromethyl group (abbreviated —$CF_3$) and the —$CH_2$—$CF_3$ group;

an alkylene group is understood to mean: a saturated and linear or branched divalent alkyl group as defined above which can comprise 1, 2, 3, 4 or 5 carbon atoms (abbreviated —($C_1$-$C_5$)alkylene-) or —$(CH_2)_{1\ to\ 5}$—. Mention may be made, for example, of the methylene (or —$CH_2$—), ethylene (or —$CH_2$—$CH_2$—) or propylene (—$CH_2$—$CH_2$—$CH_2$— or —$C(CH_3)_2$—) radicals;

an alkoxy group is understood to mean: an —O-alkyl radical where the alkyl group is as defined above. Mention may be made, as examples, of the —O—($C_1$-$C_5$)alkyl or —($C_1$-$C_5$) alkoxy groups and in particular, as (i) —O—$C_1$alkyl group, of the —O-methyl group, as (ii) —O—$C_2$alkyl group, of the —O-ethyl group, as (iii) —O—$C_3$alkyl group, of the —O-propyl group and the —O-isopropyl group, as (iv) —O—$C_4$alkyl group, of the —O-butyl group, the —O-isobutyl group and the —O-tert-butyl group, and, as (v) —O—$C_5$alkyl group, of the —O-pentyl group, the —O-isopentyl group and the —O-neopentyl group;

an aryloxy group is understood to mean: an —O-aryl radical where the aryl group is as defined below;

an aryl group is understood to mean: an aromatic cyclic group comprising 6, 7, 8, 9 or 10 carbon atoms. Mention may be made, as examples of aryl groups, of the phenyl group (abbreviated to Ph), the naphthyl group or a —$C_6H_4$-alkyl group (with the alkyl radical, as defined above, in the ortho, meta or para position of the aromatic ring system). Mention may be made, as —$C_6H_4$-alkyl group, of the —$C_6H_4$—$CH_3$ groups with $CH_3$ in the ortho, meta or para position;

an arylalkyl group is understood to mean: an aryl group, as defined above, substituted by at least one alkyl group, as defined above. Advantageously, -alkylaryl radicals are concerned. Mention may be made, for example, of benzyl, that is to say the —$CH_2$-Ph radical;

an alkoxyalkyl group is understood to mean: a radical of the formula -alkylene-O-alkyl, where the alkyl and alkylene groups, comprising the same carbon number or not comprising the same carbon number, are as defined above. Mention may be made, as examples, of the —($C_1$-$C_5$)alkylene-O— ($C_1$-$C_5$)alkyl groups with —($C_1$-$C_5$)alkylene- and —($C_1$-$C_5$) alkyl as defined above;

a heteroaryl group is understood to mean: an aromatic cyclic group comprising 2, 3, 4 or 5 carbon atoms and comprising 1, 2 or 3 heteroatoms, which can be chosen from the nitrogen atom, the oxygen atom and the sulphur atom, independently of one another, so as to be identical or different, when they are 2 in number, or independently of one another, so as to be identical or different, when they are 3 in number. Mention may be made of the pyridyl, furanyl or pyrrolyl group;

a cycloalkyl group is understood to mean: a cyclic alkyl group which can comprise 3, 4, 5 or 6 carbon atoms, also abbreviated —($C_3$-$C_6$)cycloalkyl. Mention may be made, as examples, of the cyclopropyl, cyclobutyl, cyclopentyl or cyclohexyl groups;

a heterocycloalkyl is understood to mean: a cyclic and optionally bridged alkyl group comprising 5, 6 or 7 carbon atoms and comprising 1, 2 or 3 heteroatoms which can be chosen, independently of one another, so as to be identical or different, when they are 2 in number, or independently of one another, so as to be identical or different, when they are 3 in number, from the nitrogen atom, the oxygen atom and the sulphur atom. Mention may in particular be made of the piperidinyl, piperazinyl, pyrrolidinyl, hexamethyleneimino, morpholinyl or 1,1-dioxidotetrahydrothienyl group;

an alkyleneaminoalkyl group is understood to mean: a group of formula -alkylene-N(alkyl)$_2$, where the alkylene and alkyl groups, comprising the same carbon number or not comprising the same carbon number, are as defined above. The two alkyl groups can comprise a different carbon number with respect to one another. Mention may be made, as examples, of the —(C$_1$-C$_5$)alkylene-N[(C$_1$-C$_5$)alkyl]$_2$ groups, with —(C$_1$-C$_5$)alkylene- and —(C$_1$-C$_5$)alkyl as defined above. Mention may advantageously be made of the —(CH$_2$)$_3$N[(CH$_2$)$_3$CH$_3$]$_2$ group;

an alkene group is understood to mean: a group of formula —C$_n$H$_{2n}$, where n is a natural integer greater than or equal to 2, which group can be linear or branched and which is characterized by the presence of at least one covalent double bond between two of its carbon atoms; mention may be made of the ethylene group or the but-1,3-diene group;

an alkyne group is understood to mean: a group of formula C$_n$H$_{2n-2}$, where n is a natural integer greater than or equal to 2, which group can be linear or branched and which is characterized by the presence of at least one covalent triple bond between two of its carbon atoms. Mention may be made of an acetylene group, a but-1-yne group or a dimethylacetylene group.

According to one embodiment, in the said ketobenzofuran derivative of formula (I) according to the invention:
G1 represents a C$_1$-C$_8$ alkyl group; and/or
G3 represents an —NHSO$_2$Rc group chosen from —NHSO$_2$alkyl groups and —NHSO$_2$aryl groups; and/or
Rc represents a methyl, ethyl, n-propyl, isopropyl, n-butyl, sec-butyl or tert-butyl group; and/or
G5 represents an —ORb group with Rb chosen from -alkyleneaminoalkyl groups, and/or
Ra represents a substituent chosen from a hydrogen atom, halogen atoms and alkyl groups, and/or
na is an index equal to 1 or 4.

According to another embodiment, in the said ketobenzofuran derivative of formula (I) according to the invention:
G1 represents an n-butyl group; and/or
G3 represents an —NHSO$_2$CH$_3$ group, and/or
G5 represents an —ORb group with Rb representing a 3-(di(n-butyl)amino)propyl group; and/or
Ra represents a substituent chosen from a hydrogen atom and na is an index equal to 4.

According to another embodiment, the process according to the invention makes possible the synthesis of ketobenzofuran derivatives of formula (I) where:
G1 represents a linear or branched C$_1$-C$_8$ alkyl group; or
G1 represents a linear or branched C$_1$-C$_4$ alkyl group; or
G1 represents a methyl, ethyl, n-propyl, isopropyl, n-butyl, sec-butyl or tert-butyl group; or
G1 represents an n-butyl group;
and/or
G3 represents (i) an —NHSO$_2$Rc group or (ii) an —NHRc group, where Rc represents a linear or branched C$_1$-C$_8$ alkyl group; or
G3 represents (i) an —NHSO$_2$Rc group or (ii) an —NHRc group, where Rc represents a linear or branched C$_1$-C$_4$ alkyl group; or
G3 represents (i) an —NHSO$_2$Rc group or (ii) an —NHRc group, where Rc represents a methyl, ethyl, n-propyl, isopropyl, n-butyl, sec-butyl or tert-butyl group; or
G3 represents an —NHSO$_2$CH$_3$ group; or
G3 represents an —NHSO$_2$aryl group;
and/or
G5 represents an —ORb group with Rb chosen from -alkyleneaminoalkyl groups; or G5 represents an —ORb group with Rb representing a 3-(di(n-butyl)amino)propyl group;
and/or
Ra represents a substituent chosen from a hydrogen atom, halogen atoms and alkyl groups; or
Ra represents hydrogen;
and/or
na is an index equal to 1, 2, 3 or 4; or
na is an index equal to 1 or 4.

According to another embodiment of the process according to the invention, the group G2 of the said enaminone intermediate Y-G2 represents a group chosen from —NH—(CH$_2$)$_{nb}$—NHY groups, where
nb represents an integer from 1 to 5; or
nb is equal to 2 or 4.

According to another embodiment of the process according to the invention, the group G2 is chosen from:

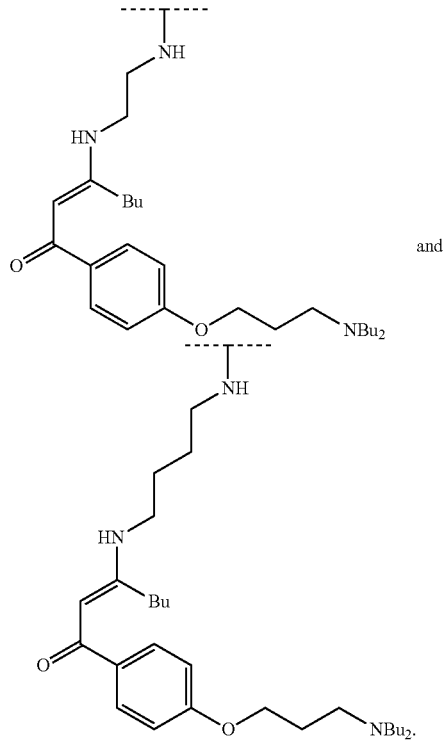

and

According to another embodiment of the process according to the invention, the group G2 of the said enaminone intermediate Y-G2 represents a group chosen from —NRdRe groups, where:
either (i) Rd is a hydrogen atom and Re is an aryl group substituted by an alkoxyalkyl or an alkyl group or Re is a tert-butyl or —C$_6$H$_4$—OCH$_3$ group,
or (ii) Rd and Re form a heterocycloalkyl with the nitrogen atom to which they are attached.

According to another embodiment of the process according to the invention, the group G4 of the said intermediate of formula (III) represents an =NSO$_2$alkyl group or an =NSO$_2$CH$_3$ group.

According to one embodiment, the enaminone intermediate of formula (II) is a compound where:
G1 represents an alkyl group; or
G1 represents a —C$_4$alkyl group; or
G1 represents an n-butyl group;
and/or
G5 represents an —ORb group with Rb chosen from aryl, arylalkyl, alkyleneaminoalkyl and heteroaryl groups, or
G5 represents an —ORb group with Rb representing a phenyl or a —C$_6$H$_4$-alkyl group.

According to one embodiment, the enaminone intermediate of formula (II) is a compound of formula Y—NH—(CH$_2$)$_{nb}$—NHY, with:
- nb representing an integer from 1 to 10, or
- nb representing an integer from 1 to 5, or
- nb representing 2, 3 or 4;

and

Y having the formula as defined below:

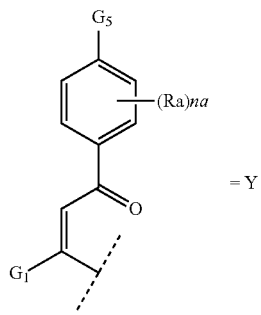

the groups G1 and G5, the substituent Ra and the index na of which are as defined above; or Y being chosen from:

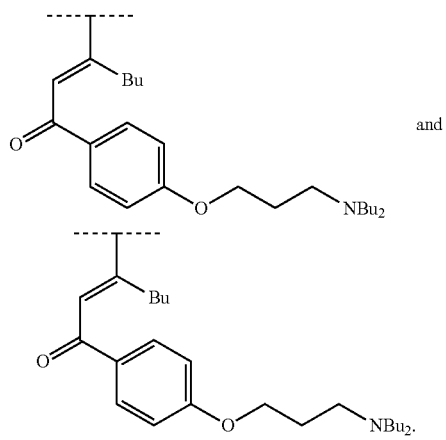

According to one embodiment, the enaminone intermediate of formula (II) or (II') is a compound chosen from the compounds of following formulae (II'a), (II'b), (II'c) and (II'd):

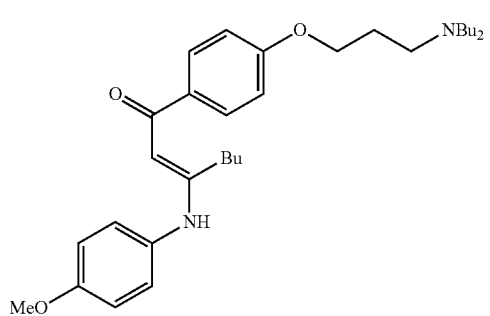

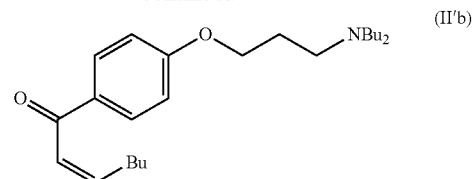

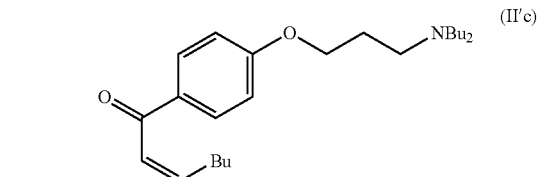

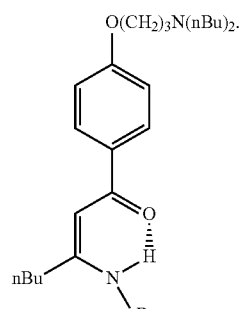

The compounds (II'b) and (II'd) are particularly advantageous.

According to one embodiment, the diketone intermediate of formula (V) is a compound where:
- G1 represents an alkyl group, or
- G1 represents a —C$_4$alkyl group, or
- G1 represents an n-butyl group;

and/or
- G5 represents a halogen atom or an —ORb group, where Rb represents an alkyl, arylalkyl, haloalkyl, aryl, heteroaryl, cycloalkyl or heterocycloalkyl group or an -alkyleneaminoalkyl group, with the exception of the —OCH$_3$ and —CH$_2$C$_6$H$_5$ groups, or G5 represents an —ORb group with Rb chosen from -alkyleneaminoalkyl groups, or G5 represents an —O(CH$_2$)$_3$—N(C$_4$H$_9$)$_2$ group.

According to one embodiment, the diketone intermediate of formula (V) is a compound (Va) of following formula:

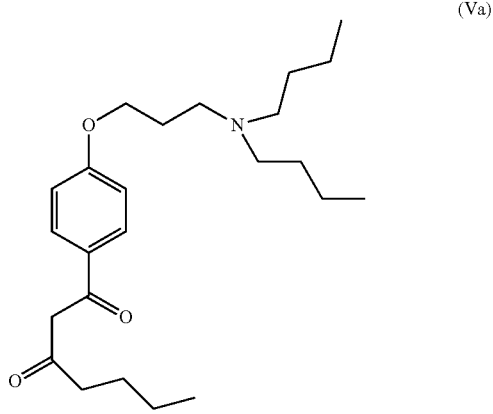 [SMILES: CCCCC(=O)CC(=O)c1ccc(OCCCN(CCCC)CCCC)cc1]

(Va)

According to one embodiment of the process according to the invention, G5 represents, in the compounds of formula (I) and/or (II) and/or (V) according to the invention:
- a fluorine atom; or
- an —ORb group with Rb representing:
  - a hydrogen atom,
  - a methyl group,
  - a phenyl group,
  - a benzyl group, or
  - a —(C$_1$-C$_5$)alkylene-N[(C$_1$-C$_5$)alkyl]$_2$ group or a —(C$_1$-C$_5$)alkylene-N$^+$H[(C$_1$-C$_5$)alkyl]$_2$ group, with —(C$_1$-C$_5$)alkylene- representing —CH$_2$—, —(CH$_2$)$_2$—, —(CH$_2$)$_3$—, —(CH$_2$)$_4$— or —(CH$_2$)$_5$— and the —(C$_1$-C$_5$)alkyl groups, which are identical or different, representing, independently of one another, a (i) —C$_1$alkyl group, for example the methyl group, a (ii) —C$_2$alkyl group, for example the ethyl group, a (iii) —C$_3$alkyl group, for example the n-propyl group or the isopropyl group, a (iv) —C$_4$alkyl group, for example the n-butyl, isobutyl or tert-butyl group, or a (v) —C$_5$alkyl group, for example the n-pentyl or isopentyl group, advantageously, —ORb represents an —O(CH$_2$)$_3$—N(n-butyl)$_2$ group.

According to one embodiment of the process according to the invention, the ketobenzofuran of formula (I) according to the invention is characterized by:
- a group G5 chosen from a fluorine atom or an —OH, —OCH$_3$, —OC$_6$H$_5$, —O—CH$_2$—C$_6$H$_5$ and —O(CH$_2$)$_3$—N(nBu)$_2$ group,
and/or
- a group G1 representing an nBu group,
and/or
- a group G3 chosen from the —NHS(O)$_2$CH$_3$ and —NHS(O)$_2$C$_6$H$_5$ groups;
and/or
- a group Ra being hydrogen and an index na representing 4.

According to one embodiment, the enaminone (II) according to the invention is characterized by:
- a group G5 chosen from a fluorine atom or an —OH, —OCH$_3$, —OC$_6$H$_5$, —O—CH$_2$—C$_6$H$_5$ and —O(CH$_2$)$_3$—N(nBu)$_2$ group,
and/or
- a group G1 representing an nBu group,
and/or
- a group G2 chosen from (i) —NH—(CH$_2$)$_{nb}$—NHY groups, with nb representing an integer from 1 to 10, advantageously an integer from 1 to 5; more advantageously still, nb represents 2 or 4; and Y representing the part of the molecule (II), and (ii) —NRdRe groups, with Rd and Re as defined above, at least one being a hydrogen atom; advantageously, Rd is a hydrogen atom and Re is an aryl group, advantageously an optionally substituted phenyl group, or an alkyl group; more advantageously still, G2 represents an —NH-tert-butyl or

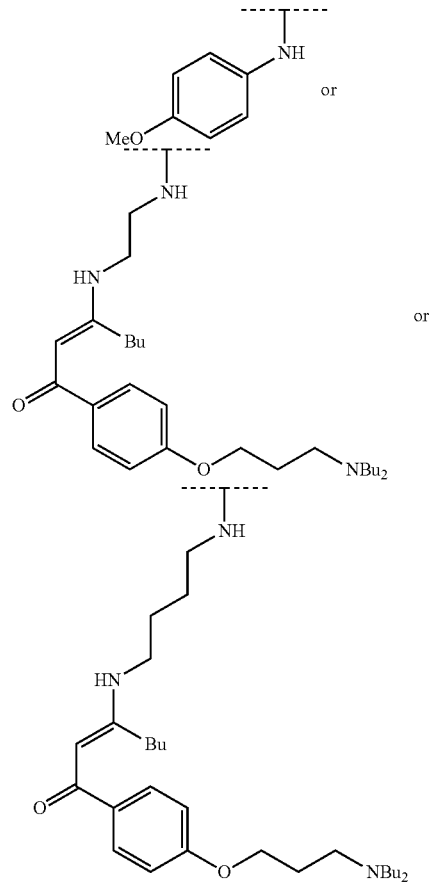

group,
and/or
- a group Ra being hydrogen and an index na representing 4.

According to one embodiment, the compound (V) according to the invention comprises:
- a group G5 chosen from a fluorine atom or a —OH, —OCH$_3$, —OC$_6$H$_5$, —O—CH$_2$—C$_6$H$_5$ and —O(CH$_2$)$_3$—N(nBu)$_2$ group,
and/or
- a group G1 representing an nBu group,
and/or
- a group Ra being hydrogen and an index na representing 4.

According to one embodiment, the diketone of formula (V) according to the invention is characterized by:
- Ra and na being as defined above;
- G1 representing an alkyl group; advantageously, G1 represents a —C$_4$alkyl group; more advantageously still, G1 represents the n-butyl group; and
- G5 representing a halogen atom or an —ORb group, where Rb represents a hydrogen atom, an alkyl, arylalkyl, haloalkyl, aryl, heteroaryl, cycloalkyl or heterocycloalkyl group or an -alkyleneaminoalkyl group, with the exception of the fluorine atom and the —OH, —OCH$_3$ and —CH$_2$C$_6$H$_5$ groups; advantageously, G5 represents an —ORb group with Rb chosen from -alkyleneaminoalkyl groups; more advantageously still, G5 represents an —O(CH$_2$)$_3$—N(C$_4$H$_9$)$_2$ group.

The following Schemes 2 and 3 relate respectively to the synthesis of the ketobenzofuran of formula (I) and in particular of the ketobenzofuran of formula (I') according to the invention.

Scheme 2

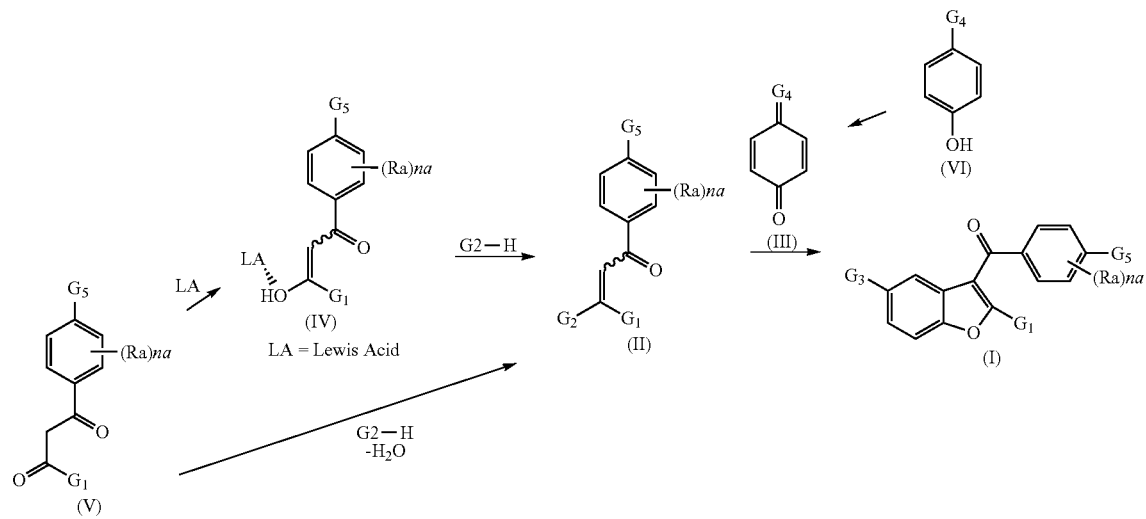

These syntheses require the production of the diketone (V) in Scheme 2 with Ra, na, G1 and G5 as defined above and of the diketone (V') in Scheme 3 with G1 and Rb as defined above. The synthesis of the diketone (V) and in particular of the diketone (V') can be carried out from commercially available compounds, such as 4-hydroxyacetophenone, and according to chemical reactions known to a person skilled in the art.

Scheme 3

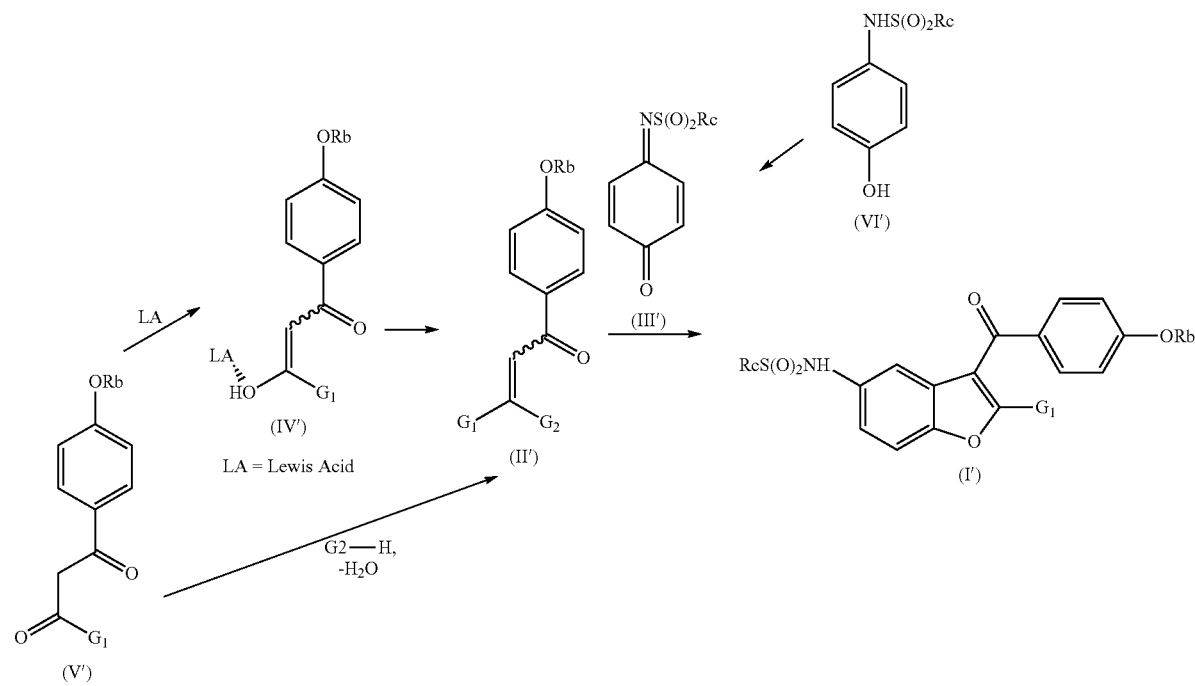

A first stage can consist in forming a complex between the said diketone (V) and in particular the diketone (V') and a Lewis acid (abbreviated LA), the latter optionally being introduced into the reaction medium in a form precomplexed with a solvent. A ketoenol complex (IV) or (IV') with the said Lewis acid (abbreviated LA), as represented respectively in Schemes 2 and 3, is then obtained, G1, Ra, na, nb and G5 being as defined above for the compounds (V) or (V').

Mention may be made, for example, as Lewis acid in accordance with the invention of $BF_3$ and titanium isopropoxide ($Ti(OiPr)_4$). Advantageously, the Lewis acid $BF_3$ is used in the form of a $BF_3.Et_2O$ complex.

This complexing of the diketone (V) or (V') with the said Lewis acid generally takes place in an aprotic solvent and can be carried out at ambient temperature. It generally lasts approximately 20 hours in order to be complete but the reaction can be halted when all the diketone has disappeared.

Mention may be made, for example, as aprotic solvent appropriate for this complexing stage in accordance with the invention, of dichloromethane and toluene.

A second stage subsequently consists in forming, for Scheme 2, the enaminone (II) and, for Scheme 3, the enaminone (II'), with G2, G1, Ra, Rb, na and G5 as defined above.

The formation of the said enaminone (II) or (II') can be carried out by 1,4 nucleophilic addition to respectively the complexed ketoenol (IV) or (IV') of a nucleophilic amine G2-H, followed by an elimination. The reaction generally takes place with an excess of nucleophilic amine G2-H and can be carried out at ambient temperature. It generally lasts approximately 20 hours.

Another alternative to the first stage and the second stage can consist in optionally bringing the said diketone (V) or (V') and an appropriate acid together beforehand, in order to form the corresponding ketoenol, and in reacting a nucleophilic amine G2-H by 1,4 nucleophilic addition to the diketone (V) or (V') or, if appropriate, the ketoenol formed under the action of the said acid, while removing the water formed. This water formed has to be withdrawn from the reaction medium either by removing it by azeotropic distillation with an appropriate reaction solvent using a Dean and Stark apparatus or by trapping it with a dehydrating agent, in order to direct the reaction towards the formation of the enaminone, respectively (II) and (II'). This alternative has the advantage of being able to synthesize the intermediates (II) and (II') in a single stage from the intermediates (V) and (V') respectively.

Mention may be made, as appropriate acid, of para-toluenesulphonic acid, camphorsulphonic acid, sulphuric acid and hydrochloric acid.

Mention may be made, as appropriate dehydrating agent, of $MgSO_4$, $CaCl_2$ and silica gel.

According to the two synthetic alternatives which can be used and which both result in the enaminone (II) or (II'), the amine G2-H can, for example, be butylenediamine, t-butylamine, p-anisidine and ethylenediamine, but all the other amines for which the group G2 is as defined above may be suitable. They can be primary or secondary amines G2-H. Advantageously, t-butylamine or p-anisidine is concerned.

Mention may be made, as reaction solvent for this second stage or the alternative to the first and to the second stage, of toluene, dichloromethane, acetonitrile and monochlorobenzene.

At the same time, (i) the p-quinone (III) with G4 as defined above, in the case of the process of the synthesis of (I), and (ii) the p-quinone (III') with Rc as defined above, in the case of the process for the synthesis of (I'), are obtained by oxidation respectively (i') of the phenol (VI) with G3 as defined above, in the case of the process of the synthesis of (I), and (ii') of the phenol (VI') with Rc as defined above, in the case of the process of the synthesis of (I'). Advantageously, this oxidation is generally carried out in the presence of manganese oxide ($MnO_2$) in acetic acid, according to procedures well known to a person skilled in the art.

A Nenitzescu reaction subsequently takes place between the p-quinone intermediate (III) or (III') and the enaminone intermediate (II) or (II') respectively.

This Nenitzescu reaction can take place, for example, in glacial acetic acid, as reactant and reaction solvent, and/or at ambient temperature. The reaction may prove to be very fast, with conversion in a few minutes, indeed even a few seconds. In general, the reaction is carried out in equimolar fashion: at least as many moles of p-quinone (III) or (III') are reacted with respectively at least as many moles of enaminone (II) or (II'). In the case where use is made of an enaminone (II) or (II') in the dimer form, such as, for example, the enaminones (II'b) and (II'c), the reaction can take place with at least 0.5 mol of the said enaminone (II) or (II') per at least 1 mol of p-quinone quinone (III) or (III') respectively.

The ketobenzofuran (I) or (I') obtained can subsequently be purified by crystallization. This crystallization can take place from a mixture, such as, for example, isopropanol/aqueous HCl in the case where it is desired to obtain the said ketobenzofuran (I) or (I') according to the invention in the form of a hydrochloride salt. Alternatively, the crystallization can take place from ether or isopropanol or from a diisopropyl ether n-heptane or MTBE/n-heptane mixture, in the case where it is desired to obtain the said ketobenzofuran (I) or (I') according to the invention in the base form.

One alternative consists in synthesizing an enaminone (II) or (II') in the dimer form of formula (IIx) or (II'x) respectively from the diketone (V) or (V') respectively according to Scheme 4a or 4b below, with G1, G5, Rb and nb as defined above.

For this, the diketone (V) or (V') is brought together with acid, for example para-toluenesulphonic acid, and diamine of formula $H_2N(CH_2)_{nb}NH_2$, with nb as defined above, at reflux, while removing the water formed, in a ratio of 2 mol of diketone per 2 mol of acid and 1 mol of amine. The dimers (II'b) and (II'c) defined below can thus be obtained, for example.

Scheme 4a

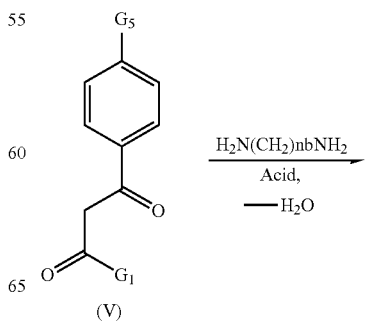

-continued

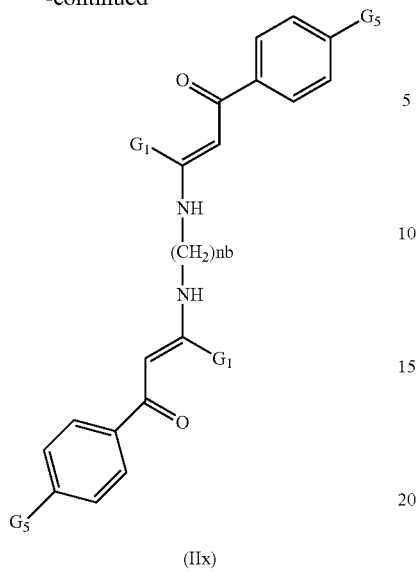

(IIx)

Scheme 4b

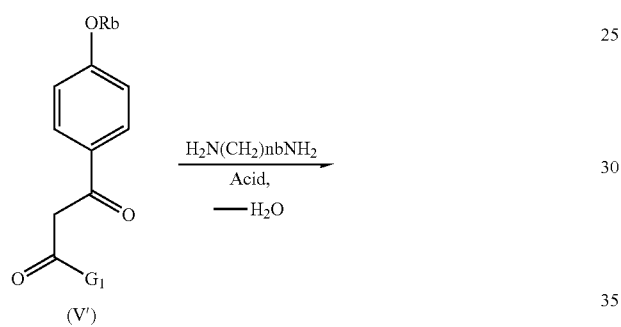

-continued

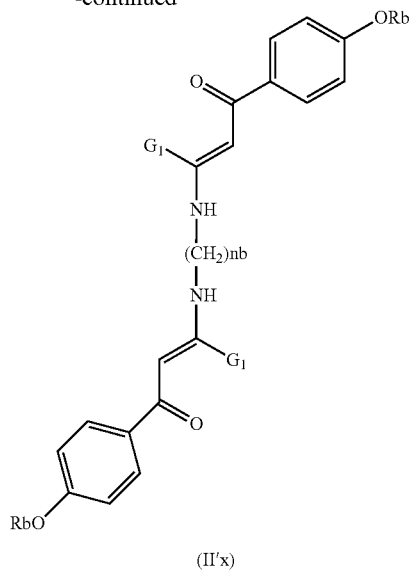

(II'x)

According to a particularly advantageous embodiment, the synthetic process according to the invention makes possible in particular the synthesis of dronedarone (D) in the base, hydrate or solvate form or in the form of one of its salts, according to Scheme 5 below. Everything which was described above relating to Schemes 2, 3, 4a and 4b, in particular the operating conditions, thus also applies for Scheme 5.

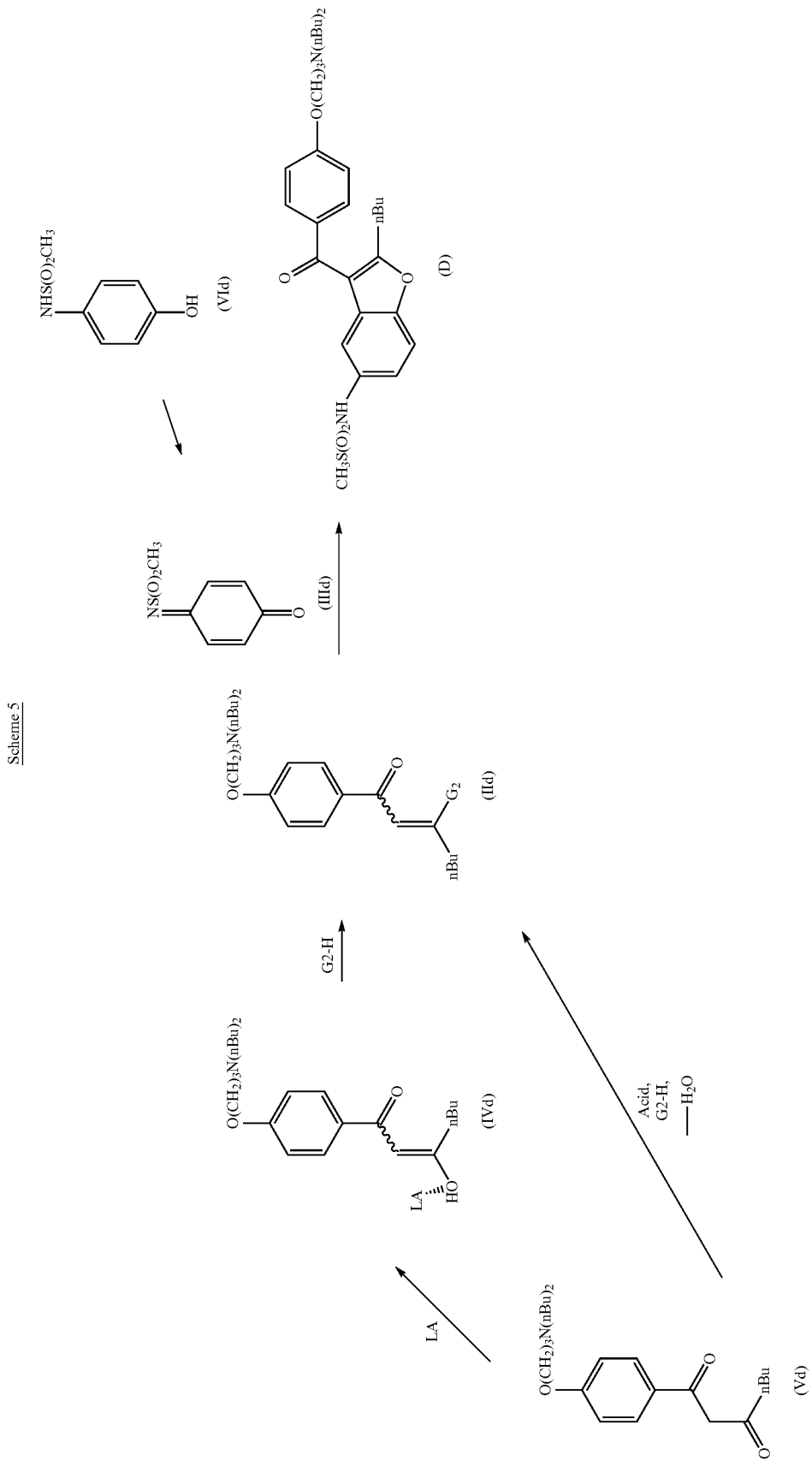

Thus, according to a particularly advantageous embodiment of the process according to the invention:
- the Lewis acid (LA) used in the reaction for the synthesis of the complex (IVd) from the diketone (Vd) is $BF_3$ or $BF_3.OEt_2$, and/or
- the G2-H used in the reaction for the synthesis of the enaminone (IId) from the ketoenol (IVd) is chosen from t-butylamine and p-anisidine, or
- the acid used in the reaction for the synthesis of the enaminone (IId), such as, for example, the enaminones (II'b) or (II'c), from the diketone (Vd) is chosen from para-toluenesulphonic acid, camphorsulphonic acid, sulphuric acid and hydrochloric acid, advantageously para-toluenesulphonic acid, and the amine G2-H is chosen from primary or secondary diamines, such as, for example, ethylenediamine and butylenediamine, the water formed during the said reaction being withdrawn from the reaction medium either by azeotropic distillation with an appropriate reaction solvent or by trapping with a dehydrating agent, advantageously by azeotropic distillation with an appropriate reaction solvent, for example toluene, or
- the amine G2-H in the reaction for the synthesis of the enaminone (IId) from the diketone (Vd) is p-anisidine, the water formed during the said reaction being withdrawn from the reaction medium either by azeotropic distillation with an appropriate reaction solvent or by trapping with a dehydrating agent, advantageously by azeotropic distillation with an appropriate reaction solvent, for example toluene.

According to one embodiment of the process according to the invention, the Nenitzescu reaction resulting in the production of the ketobenzofurans of formulae (I), (I') and (D) involves the enaminones (II), (II') and (IId) respectively with the quinonimines (III), (III') and (IIId) respectively. In addition, this Nenitzescu reaction is advantageously carried out with glacial acetic acid and/or the reaction is advantageously carried out at ambient temperature.

According to one embodiment of the process according to the invention, a stage of crystallization of the ketobenzofuran (I), (I') or (D) obtained is carried out, on conclusion of the said process:
- from an isopropanol/aqueous HCl mixture, resulting in ketobenzofuran (I), (I') or (D) respectively being obtained in the form of a hydrochloride salt, or
- from ether or from a DIPE/n-heptane mixture or from an MTBE/n-heptane mixture, resulting in the said ketobenzofuran (I), (I') or (D) being obtained in the pure base form.

The quinonimine (IIId) is synthesized from commercial products according to a reaction known to a person skilled in the art.

The process according to the invention exhibits in particular the following advantages:
- good reaction yields;
- convergent synthesis;
- limited number of synthetic stages;
- simple reactions which are technologically easy to carry out;
- no major polluting effluents;
- does not require specific industrial equipment and in particular does not require a hydrogenation stage in order to obtain an aminofunctional group in the 5 position of the benzofuran;
- common starting materials and reactants which are readily accessible and inexpensive.

The invention will now be described in more detail.

EXAMPLES

The following procedures and examples describe the preparation of intermediates for dronedarone. These procedures and examples are not limiting and serve only to illustrate the present invention.

In the following procedures and examples:
- the mass spectra are produced on a quadrupole spectrometer of Platform LCZ type (Waters) or of ZQ 4000 type (Waters) in positive electrospray ionization mode;
- the NMR (nuclear magnetic resonance) spectra are produced on a Fourier transform spectrometer (Bruker) at a temperature of 300K (exchangeable protons not recorded), the following indicators meaning: s=singlet; d=doublet; m=multiplet; br=broad; t=triplet; q=quartet; quint=quintet; sext=sextet; $C_q$=quaternary carbon; $d_6$-DMSO=deuterated dimethyl sulphoxide; $CDCl_3$=deuterated chloroform.

The NMR spectra confirm the structures of the compounds obtained according to the following examples.

In the examples which follow, the following abbreviations are used:
h: hour
min: minute
eq: equivalent
DMF: N,N-dimethylformamide
DCM: dichloromethane
DIPE: diisopropyl ether
MCH: methylcyclohexane
MTBE: methyl tert-butyl ether
MEK: methyl ethyl ketone
NMP: N-methyl-2-pyrrolidone
AcOEt: ethyl acetate
AT: ambient temperature (between approximately 20 and 25° C.)
M.p.: melting point In the general synthetic schemes which follow, the starting compounds and the reactants, when their method of preparation is not described, are commercially available or are described in the literature or else can be prepared according to methods which are described or are known to a person skilled in the art.

Example 1

Synthesis of 4-hydroxyphenylmethanesulphonamide (VId)

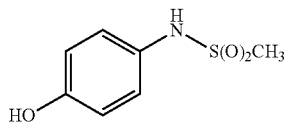

4-Aminophenol (10 g; 0.091 mol; 1 eq) is suspended in methanol (100 ml) in the presence of pyridine (7.67 ml; 0.095 mol; 1.05 eq) at 20° C. Mesyl chloride (7.16 ml; 0.091 mol; 1.05 eq) is slowly run onto the reaction medium, which then turns orange and then pink in colour. The methanol is removed by evaporating to dryness when the reaction is complete (1 h 30). The residue obtained is treated for 30 min with a dilute 1N hydrochloric acid solution (85.5 ml; 1.05 eq). The pink solid formed is filtered off and then washed with 1N HCl (30 ml) before being purified under hot conditions (45° C.) by treatment with active charcoal in ethyl acetate (30 ml). The solid obtained is washed with 1N HCl and then dried overnight at 40° C. in an oven under vacuum. As the aqueous liquors contain a great deal of mesylated product, they are extracted with ethyl acetate. The extraction liquors are treated as above. 10.4 g of sulphonamide, pale pink powder.

Isolated yield of 4-hydroxyphenylmethanesulphonamide: 67% by weight.

$^1$H NMR (400 MHz, $d_6$-DMSO): δ 3.41 (s, 3H, —SO$_2$CH$_3$); 6.72 (d, 2H, J=8.5 Hz, CH); 7.02 (d, 2H, J=8.5 Hz, CH); 9.17 and 9.39 (2*s, 2*1H, OH and NH)

$^{13}$C NMR ($d_6$-DMSO): δ 38.3 (CH$_3$); 115.5 and 124.0 (4*CH); 129.0 ($C_q$—N); 154.8 ($C_q$—O)

Example 2

Synthesis of N-(4-oxocyclohexa-2,5-dien-1-ylidene) methanesulphonamide (IIId)

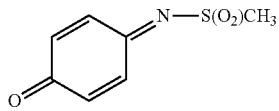

The sulphonamide (30 g; 0.16 mol; 1 eq) is oxidized in acetic acid (450 ml; 15 V) at 35° C. in the presence of manganese oxide (15.76 g; 0.179 mol; 1.12 eq). After stirring at 35° C. for 1 h 30, the reaction is complete and the medium is evaporated to dryness. The black solid obtained is taken up in dichloromethane (400 ml). The precipitate of manganese salts formed is filtered off and then washed with DCM (400 ml). The black organic phases are subsequently percolated through a bed of Florisil® (190 g) in order to give clear liquors orange in colour. After evaporation, an orange solid is obtained (18.5 g) comprising 15% of benzoquinone, which is removed by two operations of suspending in ethanol (20 ml) at 20° C.

14.9 g of a fine orange powder of N-(4-oxocyclohexa-2,5-dien-1-ylidene)methanesulphonamide are obtained.

Crude isolated yield of N-(4-oxocyclohexa-2,5-dien-1-ylidene)methanesulphonamide: 62% by weight.

Yield after purification: 50.2% by weight.

$^1$H NMR (400 MHz, d$_6$-DMSO): δ 3.41 (s, 3H, —SO$_2$CH$_3$); 6.83 (m, 2H, CH); 7.17 (m, 1H, CH); 7.84 (m, 1H, CH).

$^{13}$C NMR (d$_6$-DMSO): δ 42.5 (CH$_3$); 129.5, 135.6, 136.0, 139.9 (4*CH); 164.2 (C$_q$=N); 186.0 (C$_q$=O).

Example 3

Synthesis of the hydrochloride of the diketone 1-{4-[3-(dibutylamino)propoxy]phenyl}heptane-1,3-dione (Vd)

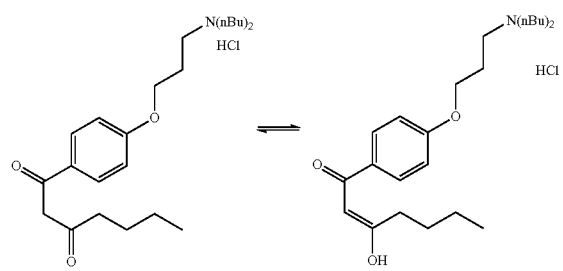

4-Hydroxyacetophenone (47.9 g, 0.35 mol, 1 eq) is dissolved in 220 ml of MEK. K$_2$CO$_3$ (53.5 g, 0.39 mmol, 1.1 eq) is added and the suspension is heated to reflux. 3-Chloro-N,N-dibutylpropylamine (82 g, 0.40 mol, 1.15 eq) is slowly introduced and then the reaction medium is maintained at reflux. When the reaction is complete, the MEK is dissolved off. 200 ml of water and 200 ml of MTBE are added at 25° C. Separation by settling is allowed to take place and the two phases are withdrawn. The aqueous phase is back extracted with MTBE and then the combined organic phases are washed with 200 ml of a 1% aqueous acetic acid solution and then 2 times 200 ml of a 5% aqueous NaCl solution. The organic phase is subsequently concentrated and the MTBE is replaced with 325 ml of NMP.

Ethyl pentanoate (58.1 ml, 0.39 mol, 1.1 eq) is added and the mixture is stirred at 5° C. MeONa (57.5 g, 1.05 mol, 3 eq) is added in portions and then the reaction medium is maintained at 20° C. At the end of the reaction, hydrolysis is carried out by running the reaction medium onto a 37% HCl solution (104.9 g, 1.05 mmol, 3 eq) at 5° C. The hydrolyzed medium is then diluted with 150 ml of water and then extracted with 3 times 200 ml of AcOEt. The combined organic phases are washed with 2 times 150 ml of water and then concentrated: the AcOEt is replaced with 300 ml of MCH. The suspension obtained is filtered and the cake is washed with MCH and then dried under vacuum at 40° C.

121.8 g of the hydrochloride of the diketone 1-{-4-[3-(dibutylamino)propoxy]phenyl}heptane-1,3-dione are then isolated in the form of a cream powder.

Isolated yield of the hydrochloride of the diketone 1-{4-[3-(dibutylamino)propoxy]phenyl}heptane-1,3-dione: 87% by weight.

Enol Form:

$^1$H NMR (400 MHz, CDCl$_3$): δ 0.94 (t, J=7.5 Hz, 3H, CH$_3$); 0.98 (t, J=7.5 Hz, 2*3H, 2*CH$_3$); 1.39 (sext, 2H, J=7.5 Hz, —CH$_2$—); 1.41 (sext, 2*2H, J=7.5 Hz, 2*—CH$_2$—); 1.66 (quint, 2H, J=7.5 Hz, —CH$_2$—); 1.81 (quint, 2*2H, J=7.5 Hz, 2*—CH$_2$—); 2.39 (t, 2H, J=7.5 Hz, —CH$_2$—CO—); 2.43 (quint, 2H, J=5 Hz, —CH$_2$—); 3.03 (m, 2*2H, 2*N—CH$_2$—); 3.22 (m, 2H, N—CH$_2$—); 4.15 (t, 2H, J=5 Hz, O—CH$_2$—); 6.10 (s, 1H, =CH—); 6.91 (d, 2H, J=9 Hz, 2*ArH); 7.86 (d, J=9 Hz, 2*1H, 2*ArH); 12.31 (br s, 2*1H, OH and NH$^+$)

$^{13}$C NMR (CDCl$_3$): δ 13.6 (2*CH$_3$); 13.9 (CH$_3$); 20.2 (2*CH$_2$); 22.4 (CH$_2$); 23.9 (CH$_2$); 25.0 (2*CH$_2$); 28.1 (CH$_2$); 38.6 (CH$_2$); 50.5 (N—CH$_2$); 52.5 (2*N—CH$_2$); 65.1 (O—CH$_2$); 95.3 (CH); 114.3 (2*CH); 128.5 (C$_q$); 129.2 (2*CH); 161.5 (C$_q$); 184.1 (C$_q$—OH); 195.1 (C=O)

Ketone Form:

$^1$H NMR (400 MHz, CDCl$_3$): δ 0.88 (t, J=7.5 Hz, 3H, CH$_3$); 0.98 (t, J=7.5 Hz, 2*3H, 2*CH$_3$); 1.30 (sext, 2H, J=7.5 Hz, —CH$_2$—); 1.41 (sext, 2*2H, J=7.5 Hz, 2*—CH$_2$—); 1.57 (quint, 2H, J=7.5 Hz, —CH$_2$—); 1.81 (quint, 2*2H, J=7.5 Hz, 2*—CH$_2$—); 2.57 (t, 2H, J=7.5 Hz, —CH$_2$—CO—); 2.43 (quint, 2H, J=5 Hz, —CH$_2$—); 3.03 (m, 2*2H, 2*N—CH$_2$—); 3.22 (m, 2H, N—CH$_2$—); 4.02 (s, 1H, —CH$_2$—); 4.17 (t, 2H, J=5 Hz, O—CH$_2$—); 6.91 (d, 2H, J=9 Hz, 2*ArH); 7.91 (d, J=9 Hz, 2*1H, 2*ArH)

$^{13}$C NMR (CDCl$_3$): δ 13.6 (2*CH$_3$); 13.9 (CH$_3$); 20.2 (2*CH$_2$); 22.2 (CH$_2$); 23.9 (CH$_2$); 25.0 (2*CH$_2$); 25.6 (CH$_2$); 43.1 (CH$_2$); 50.5 (N—CH$_2$); 52.5 (2*N—CH$_2$); 54.0 (CH$_2$); 65.3 (O—CH$_2$); 114.4 (2*CH); 130.1 (C$_q$); 131.3 (2*CH); 162.5 (C$_q$); 192.4 (C=O); 204.8 (C=O)

Example 4

(2E)-1-{4-[3-(dibutylamino)propoxy]phenyl}-3-hydroxyhept-2-en-1-one-trifluoroborane (IVd)

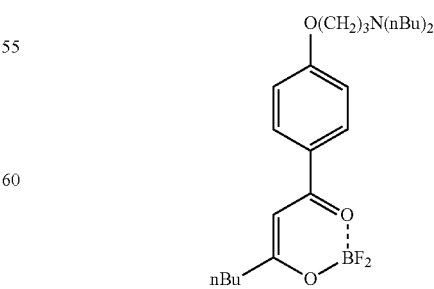

The diketone of Example 3 (23.5 g; 60 mmol; 1 eq) is dissolved at 25° C. in dichloromethane (230 ml) and then BF$_3$.Et$_2$O (23.5 ml, 181 mmol, 3 eq) is slowly added. The red solution is stirred at 25° C. until the diketone has disappeared (17 h) and is then brought to dryness by evaporation under vacuum. The red solid obtained is taken up in water in order to give, after filtration and washing operations with water and then drying in an oven (40° C., 15 mbar), an orangey yellow powder (yield obtained=30 g).

$^1$H NMR (400 MHz, CDCl$_3$): δ 0.96 (t, J=7.5 Hz, 3H, C$\underline{H}_3$); 0.99 (t, J=7.5 Hz, 2*3H, 2*C$\underline{H}_3$); 1.43 (sext, 6H, J=7.5 Hz, 3*—C$\underline{H}_2$—); 1.74 (m, 6H, 3*—C$\underline{H}_2$—); 2.32 (m, 2H, —C$\underline{H}_2$—); 2.59 (t, 2H, J=7.5 Hz, —C$\underline{H}_2$—CO—); 3.17 (m, 2*2H, 2*N—C$\underline{H}_2$—); 3.37 (m, 2H, N—C$\underline{H}_2$—); 4.19 (t, 2H, J=5.5 Hz, O—C$\underline{H}_2$—); 6.48 (s, 1H, =C$\underline{H}$—); 6.97 (d, 2H, J=9 Hz, 2*Ar$\underline{H}$); 7.51 (br s, 1H, NH$^+$); 8.01 (d, J=9 Hz, 2*1H, 2*Ar$\underline{H}$); 12.31 (br s, 2*1H, OH and NH$^+$)

$^{13}$C NMR (CDCl$_3$): δ 13.5 (2*C$\underline{H}_3$); 13.7 (C$\underline{H}_3$); 19.8 (2*C$\underline{H}_2$); 22.3 (C$\underline{H}_2$); 24.0 (C$\underline{H}_2$); 25.4 (2*C$\underline{H}_2$); 28.2 (C$\underline{H}_2$); 37.7 (C$\underline{H}_2$); 51.7 (N—C$\underline{H}_2$); 53.7 (2*N—C$\underline{H}_2$); 65.2 (O—C$\underline{H}_2$); 95.9 (CH); 115.1 (2*CH); 124.2 (C$_q$); 131.7 (2*CH); 164.1 (C$_q$); 181.7 (C$_q$—O); 194.5 (C=O)

Example 5

Synthesis of (2E,2'E)-3,3'-(1,4-butanediyldiimino)bis(1-{4-[3-(dibutylamino)propoxy]phenyl}-2-hepten-1-one) (II'c)

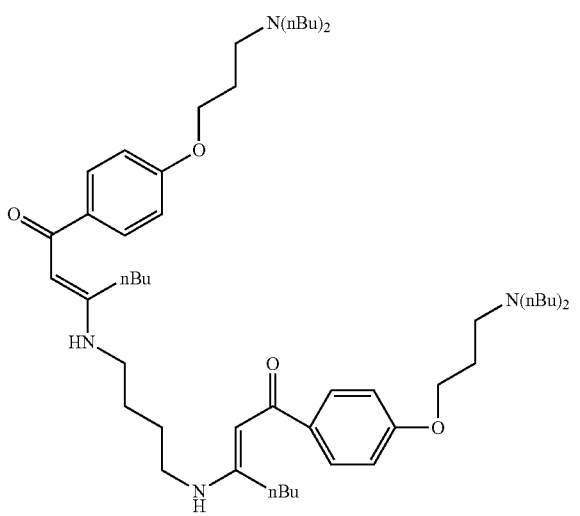

The base of the hydrochloride of the diketone of Example 3 (15 g; 35.2 mmol; 2 eq) is released in toluene (100 ml) and water (75 ml) with sodium hydrogencarbonate (3.69 g; 44 mmol; 2.5 eq). The aqueous phase is extracted with toluene (40 ml) and the combined organic phases are washed with water (40 ml). p-Toluenesulphonic acid (0.45 g; 2.6 mmol; 0.15 eq) is added to this organic solution before charging butylenediamine (1.55 g; 17.6 mmol; 1 eq). The medium is then heated at reflux, the water formed being removed using a Dean and Stark apparatus. When the reaction is complete, a slight precipitate is filtered off and the toluene liquors are evaporated to dryness. The beige solid obtained (12.7 g) is stirred in acetonitrile (65 ml) and then filtered off. After washing the cake with acetonitrile (10 ml) and then drying in an oven for 48 h, 8.2 g of pure (2E,2'E)-3,3'-(1,4-butanediyldiimino)bis(1-{4-[3-(dibutylamino)propoxy]phenyl}-2-hepten-1-one) are isolated.

Crude isolated yield of (2E,2'E)-3,3'-(1,4-butanediyldiimino)bis(1-{4-[3-(dibutylamino)propoxy]phenyl}-2-hepten-1-one): 87% by weight.

Isolated yield of (2E,2'E)-3,3'-(1,4-butanediyldiimino)bis(1-{4-[3-(dibutylamino)propoxy]phenyl}-2-hepten-1-one) after purification: 56% by weight.

$^1$H NMR (400 MHz, CDCl$_3$): δ 0.89 (t, J=7 Hz, 12H, 4*C$\underline{H}_3$); 0.95 (t, J=7.5 Hz, 2*3H, 2*C$\underline{H}_3$); 1.29 (sext, 6H, J=7 Hz, 4*—C$\underline{H}_2$—); 1.41 (quint, 6H, J=7 Hz, 4*—C$\underline{H}_2$—); 1.43 (sext, 4H, J=7.5 Hz, 2*—C$\underline{H}_2$—); 1.59 (quint, 4H, J=7.5 Hz, 2*—C$\underline{H}_2$—); 1.81 (m, 4H, 2*—C$\underline{H}_2$—); 1.91 (quint, 4H, J=6.5 Hz, 2*—C$\underline{H}_2$—); 2.30 (t, 4H, J=8 Hz, 2*—C$\underline{H}_2$—); 2.41 (t, 8H, J=7 Hz, 4*N—C$\underline{H}_2$—); 2.58 (t, 4H, J=6.5 Hz, 2*N—C$\underline{H}_2$—); 3.38 (m, 4H, 2*—C$\underline{H}_2$—); 4.04 (t, 4H, J=6.5 Hz, 2*O—C$\underline{H}_2$—); 5.63 (s, 2H, 2*=C$\underline{H}$—); 6.88 (d, 4H, J=9 Hz, 4*Ar$\underline{H}$); 7.81 (d, J=9 Hz, 4H, 4*Ar$\underline{H}$); 11.48 (t, 2H, J=5.5 Hz, 2*N$\underline{H}$)

$^{13}$C NMR (CDCl$_3$): δ 13.9 (2*C$\underline{H}_3$); 14.1 (4*C$\underline{H}_3$); 20.8 (4*C$\underline{H}_2$); 27.2 (2*C$\underline{H}_2$); 27.7 (2*C$\underline{H}_2$); 29.4 (4*C$\underline{H}_2$); 30.3 (2*C$\underline{H}_2$); 32.3 (2*C$\underline{H}_2$); 42.5 (2*C$\underline{H}_2$); 50.6 (2*N—C$\underline{H}_2$); 54.1 (4*N—C$\underline{H}_2$); 66.4 (2*O—C$\underline{H}_2$); 90.6 (2*CH); 113.9 (4*CH); 128.6 (4*CH); 133.1 (2*C$_q$); 168.3 (2*C$_q$); 187.3 (2*C=O)

Example 6

Synthesis of (2E)-1-{4-[3-(dibutylamino)propoxy]phenyl}-3-(propan-2-ylamino)hept-2-en-1-one (II'd)

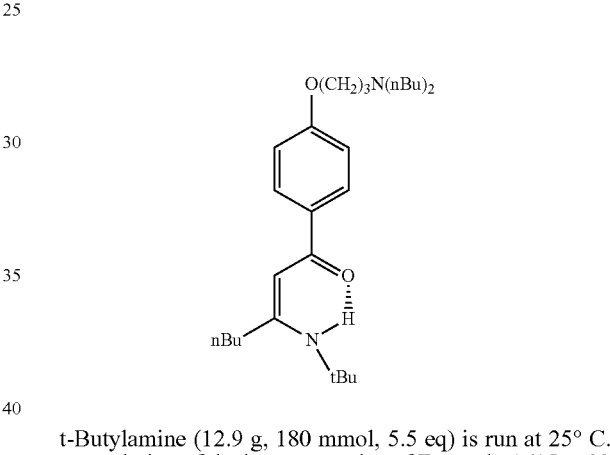

t-Butylamine (12.9 g, 180 mmol, 5.5 eq) is run at 25° C. onto a solution of the boron complex of Example 4 (15 g, 33 mmol, 1.0 eq) in acetonitrile (100 ml). A precipitate is gradually formed, giving a red suspension which has to be stirred at 25° C. for 20 h. The complexed t-butylamine precipitate is filtered off and the liquors are evaporated to dryness to give an opaque red syrup. After taking up in dichloromethane (100 ml) and then washing with water (5×50 ml), the solution is again evaporated and a red oil is obtained (13.9 g).

Crude isolated yield of (2E)-1-{4-[3-(dibutylamino)propoxy]phenyl}-3-(propan-2-ylamino)hept-2-en-1-one: 95.2% by weight.

Purification by preparative chromatography on silica gel of 4.5 g of crude product with toluene (95)/methanol (5) as elution solvent makes it possible to isolate 2.8 g of enaminone of satisfactory purity (NMR assay >90%).

Isolated yield of (2E)-1-{4-[3-(di butylamino)propoxy]phenyl}-3-(propan-2-ylamino)hept-2-en-1-one after purification: 59% by weight.

$^1$H NMR (400 MHz, CDCl$_3$): δ 0.95 (t, J=7.5 Hz, 6H, 2*C$\underline{H}_3$); 0.97 (t, J=7.5 Hz, 3H, C$\underline{H}_3$); 1.37 (sext, 4H, J=7.5 Hz, 2*—C$\underline{H}_2$—); 1.45 (m, 2H, —C$\underline{H}_2$—); 1.46 (s, 9H, 3*C$\underline{H}_3$); 1.64 (m, 4H, 2*—C$\underline{H}_2$—); 1.65 (m, 2H, —C$\underline{H}_2$—); 2.17 (m, 2H, —C$\underline{H}_2$—); 2.45 (t, 2H, J=8 Hz, —C$\underline{H}_2$—); 2.95 (m, 4H, 2*N—C$\underline{H}_2$—); 3.15 (m, 2H, N—C$\underline{H}_2$—); 4.09 (t, 2H, J=5.5 Hz, O—C$\underline{H}_2$—); 5.58 (s, 1H, =C$\underline{H}$—); 6.86 (d, 2H, J=9 Hz, 2*Ar$\underline{H}$); 7.80 (d, J=9 Hz, 2H, 2*Ar$\underline{H}$); 11.98 (s, 1H, N$\underline{H}$)

$^{13}$C NMR (CDCl$_3$): δ 13.7 (2*C$\underline{H}_3$); 13.9 (C$\underline{H}_3$); 20.1 (2*C$\underline{H}_2$); 23.0 (C$\underline{H}_2$); 24.8 (C$\underline{H}_2$); 26.3 (2*C$\underline{H}_2$); 31.3 (3*C$\underline{H}_3$);

31.9 (C$\underline{H}_2$); 32.7 (C$\underline{H}_2$); 51.3 (N—C$\underline{H}_2$); 52.6 (C$_q$); 53.7 (2*N—C$\underline{H}_2$); 65.0 (O—C$\underline{H}_2$); 91.3 (CH); 113.8 (2*CH); 128.6 (2*CH); 134.1 (C$_q$); 160.1 (C$_q$); 170.0 (N—C$_q$=); 186.0 (C=O)

Example 7

Synthesis of N-(2-butyl-3-{4-[3-(dibutylamino)propoxy]benzoyl}-1-benzofuran-5-yl)methanesulphonamide and N-(2-butyl-3-{4-[3-(dibutylamino)propoxy]benzoyl}-1-benzofuran-5-yl) methanesulphonamide hydrochloride (D)

The dimer of Example 5 (4 g; 4.8 mmol; 0.5 eq) is dissolved in glacial acetic acid (28 ml). The quinoneimine of Example 2 (1.78 g; 9.6 mmol; 1 eq) is charged to the medium at 20° C. The reaction is immediate and dronedarone base is obtained. After having evaporated the acetic acid, the reaction medium is taken up in dichloromethane (50 ml). It is washed with a 10% w/w potassium hydrogencarbonate solution (25 ml) and then with dilute HCl (3×25 ml). The DCM is evaporated and the crude product obtained is purified by crystallization at 40° C. from isopropanol (15 ml). Dronedarone (D) in the hydrochloride form is obtained in the form of a white powder (2.64 g).

Isolated yield of dronedarone in the form of the hydrochloride salt: 47% by weight.

Example 8

Synthesis of N-(2-butyl-3-{4-[3-(dibutylamino)propoxy]benzoyl}-1-benzofuran-5-yl)methanesulphonamide and N-(2-butyl-3-{4-[3-(dibutylamino)propoxy]benzoyl}-1-benzofuran-5-yl) methanesulphonamide hydrochloride (D)

The enaminone of Example 6 (2.3 g, 5.2 mmol, 1 eq) is dissolved in glacial acetic acid (11.5 ml). The quinoneimine of Example 2 (0.96 g, 5.2 mmol, 1 eq) is charged to the medium at 20° C. The reaction is immediate. After having evaporated the acetic acid, the reaction medium is taken up in dichloromethane (50 ml). The organic phase is washed with a potassium hydrogencarbonate solution (25 ml, 10% w/w) and then washed with dilute HCl (3×25 ml). After the evaporating solvent, the crude product obtained is purified by crystallization from isopropanol (9.5 ml) after addition at 50° C. of 35% HCl (43 mg, 4.2 mmol). The product is obtained in the form of a white powder (weight obtained=2.2 g).

Isolated yield of dronedarone in the form of a hydrochloride salt: 73% by weight.

$^1$H NMR (400 MHz, CDCl$_3$): δ 0.87 (t, J=7.5 Hz, 3H, CH$_3$); 0.93 (t, J=7.5 Hz, 6H, 2*CH$_3$); 1.30-1.41 (m, 6H, 3*—C$\underline{H}_2$); 1.68-1.79 (m, 6H, 3*—C$\underline{H}_2$—); 2.37-2.40 (m, 2H, —O—CH$_2$); 2.87 (s, 3H, C$\underline{H}_3$—S—); 2.90 (t, J=7.5 Hz, 2H, —C$\underline{H}_2$—); 3.04 (m, 4H, 2*C$\underline{H}_2$—NH$^+$); 3.24 (m, 2H, NH$^+$—C$\underline{H}_2$—); 4.17 (t, J=6 Hz, 2H, —CH$_2$—O); 6.88 (d, J=9 Hz, 2H, 2*ArH); 7.22 (d, J=2.5 Hz, 1H, ArH); 7.33 (dd, J=9 Hz and 2.5 Hz, 1H, ArH); 7.37 (d, J=9 Hz, 1H, ArH); 7.74 (d, J=9 Hz, 2H, 2*ArH); 8.24 (s, 1H, NH$^+$)

$^{13}$C NMR (d$_6$-DMSO): δ 13.5 and 13.7 (3*C$\underline{H}_3$); 20.1 (2*C$\underline{H}_2$); 22.3 (C$\underline{H}_2$); 23.7 (C$\underline{H}_2$); 25.0 (2*C$\underline{H}_2$); 27.9 (C$\underline{H}_2$); 30.1 (C$\underline{H}_2$); 38.7 (SO$_2$—C$\underline{H}_3$); 50.3 (N—C$\underline{H}_2$); 52.4 (2*N—C$\underline{H}_2$); 65.0 (O—C$\underline{H}_2$); 111.5 (CH); 114.4 (2*CH); 115.6 (CH); 116.7 (C$_q$); 120.0 (CH); 127.8 (C$_q$); 131.6 (2*CH); 132.1 (C$_q$); 133.2 (C$_q$); 151.5 (C$_q$); 161.9 (C$_q$); 166.3 (C$_q$); 190.0 (C=O)

Example 9

Synthesis of the hydrochloride of (2E)-1-{4-[3-(dibutylamino)propoxy]phenyl}-3-[(4-methoxyphenyl)amino]-2-hepten-1-one (II'a)

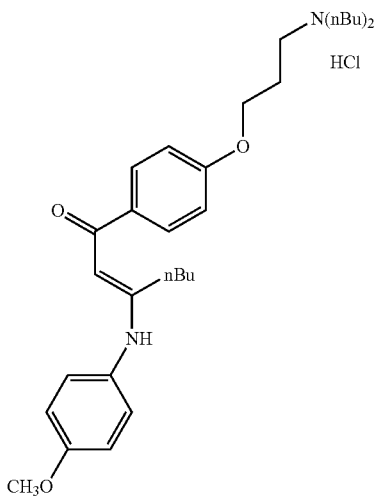

0.5 g of the diketone of Example 3 is charged to a reactor with 5 ml of toluene and 160 mg of p-anisidine. This mixture is heated so as to remove the water by azeotropic distillation using Dean and Stark apparatus.

When the reaction is complete, the reaction medium is concentrated, cooled to 20° C. and evaporated to dryness. The solid obtained is taken up in ether and then filtered off. After drying in a vacuum oven, 380 mg of product are recovered in the form of a cream powder.

Isolated yield of (2E)-1-{4-[3-(dibutylamino)propoxy]phenyl}-3-[(4-methoxyphenyl)amino]-2-hepten-1-one hydrochloride: 56% by weight $^1$H NMR (400 MHz, d$_6$-DMSO): δ 0.78 (t, J=7.5 Hz, 3H, C$\underline{H}_3$); 0.91 (t, J=7.5 Hz, 6H, 2*C$\underline{H}_3$); 1.23 (sext, 2H, J=7.5 Hz, —C$\underline{H}_2$—); 1.32 (sext, 4H, J=7.5 Hz, 2*—C$\underline{H}_2$—); 1.43 (quint, 2H, J=7.5 Hz, —CH$_2$—); 1.64 (m, 4H, 2*—C$\underline{H}_2$—); 2.15 (m, 2H, —CH$_2$—); 2.37 (m, 2H, —CH$_2$—); 3.01 (m, 4H, 2*N—CH$_2$—); 3.17 (m, 2H, N—CH$_2$—); 3.77 (s, 3H, O—CH$_3$); 4.14 (t, 2H, J=6 Hz, O—CH$_2$—); 5.98 (s, 1H, =CH—); 6.98 (d, 2H, J=9 Hz, 2*ArH); 7.00 (d, 2H, J=9 Hz, 2*ArH); 7.19 (d, 2H, J=9 Hz, 2*ArH); 7.90 (d, J=9 Hz, 2H, 2*ArH); 10.55 (br s, 1H, NH$^+$); 12.91 (s, 1H, NH)

What is claimed is:
1. An enaminone chosen from the compounds of following formulae (II'a), (II'b), (II'c) and (II'd):
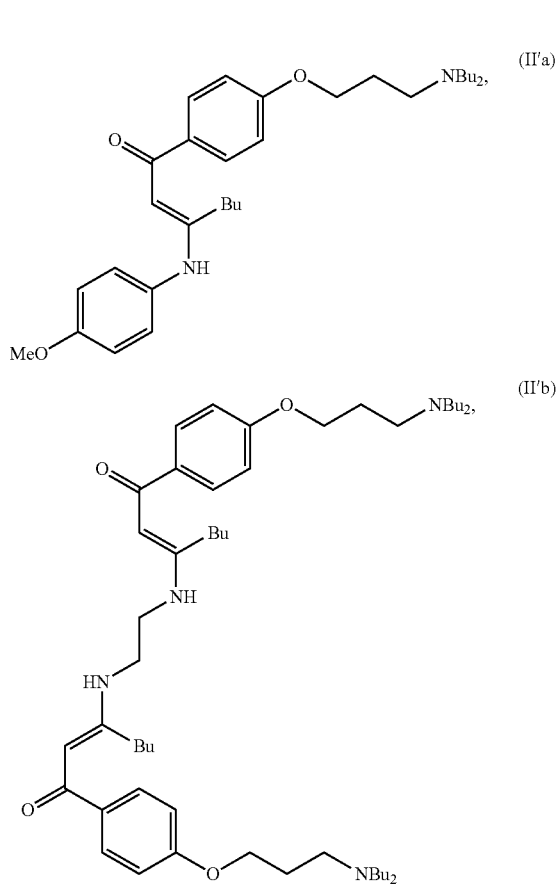
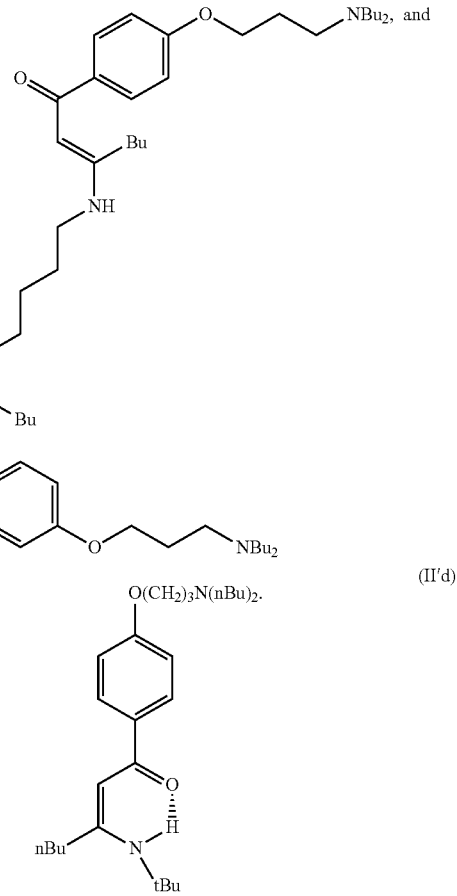

$^{13}$C NMR (d$_6$-DMSO): δ 13.4 (C$\underline{H}_3$); 13.5 (2*C$\underline{H}_3$); 19.4 (2*C$\underline{H}_2$); 21.7 (C$\underline{H}_2$); 29.5 (C$\underline{H}_2$); 31.1 (C$\underline{H}_2$); 51.7 (2*N—C$\underline{H}_2$); 64.9 (O—C$\underline{H}_2$); 91.3 (CH); 114.0 (2*CH); 114.4 (2*CH); 126.4 (2*CH); 128.7 (2*CH); 130.7 (C$_q$); 132.3 (C$_q$); 157.3 (C$_q$); 160.4 (C$_q$); 166.5 (N—C$_q$=); 186.1 (C=O)